US011160507B2

(12) United States Patent
Gray et al.

(10) Patent No.: US 11,160,507 B2
(45) Date of Patent: Nov. 2, 2021

(54) INFORMATION AND PASSIVE BIOMETRIC SYSTEMS AND METHODS

(71) Applicant: Palatiumcare, Inc., Sheboygan, WI (US)

(72) Inventors: Daniel Gordon Gray, Sheboygan, WI (US); Lucas Alexander Narbatovics, Fond du Lac, WI (US)

(73) Assignee: Palatiumcare, Inc., Sheboygan, WI (US)

( * ) Notice: Subject to any disclaimer, the term of this patent is extended or adjusted under 35 U.S.C. 154(b) by 0 days.

(21) Appl. No.: 16/760,012

(22) PCT Filed: Oct. 30, 2018

(86) PCT No.: PCT/US2018/058239
§ 371 (c)(1),
(2) Date: Apr. 28, 2020

(87) PCT Pub. No.: WO2019/089615
PCT Pub. Date: May 9, 2019

(65) Prior Publication Data
US 2020/0345307 A1 Nov. 5, 2020

Related U.S. Application Data

(60) Provisional application No. 62/578,892, filed on Oct. 30, 2017.

(51) Int. Cl.
*A61B 5/00* (2006.01)
*A61B 5/117* (2016.01)
*G09G 3/3208* (2016.01)

(52) U.S. Cl.
CPC ............ *A61B 5/6891* (2013.01); *A61B 5/002* (2013.01); *A61B 5/117* (2013.01); *A61B 5/6889* (2013.01);
(Continued)

(58) Field of Classification Search
CPC ....... A61B 5/6891; A61B 5/117; A61B 5/746; F21V 33/0012
(Continued)

(56) References Cited

U.S. PATENT DOCUMENTS 8,456,293 B1 6/2013 Trundle
9,193,359 B2 * 11/2015 Hui .......................... B60R 16/02
(Continued)

OTHER PUBLICATIONS

International Search Report and Written Opinion in International Application No. PCT/US2018/058239, dated Feb. 27, 2019 (12 pages).

*Primary Examiner* — John A Tweel, Jr.
(74) *Attorney, Agent, or Firm* — Nixon Peabody LLP; Justin D. Swindells

(57) ABSTRACT

Information and passive biometric capture systems and methods. The information system includes a housing having a cavity configured to receive tangible items therein. A transparent, touch-sensitive display device is positioned over the cavity and configured such that in response to pixels of the display being black, the tangible items behind the black pixels are visible through the transparent display. A controller is programmed to receive from a remote server an alarm signal, and in response thereto, cause the display to change its state to indicate an alarm condition on the display. In response to receiving an input from the touch-sensitive display, a keypad is displayed, and inputs thereon are communicated to the remote server. The display can also display personal photographs stored in the memory device. A passive biometric capture system includes a chair with pressure-sensitive sensors embedded within areas contacted by a person sitting in the chair to form a unique passive biometric signature for each person and thereby differentiate among different people who sit in the same chair.

6 Claims, 20 Drawing Sheets

(52) U.S. Cl.
CPC ............... *A61B 5/742* (2013.01); *A61B 5/746* (2013.01); *G09G 3/3208* (2013.01)

(58) Field of Classification Search
USPC ...................................................... 340/573.1
See application file for complete search history.

(56) References Cited

U.S. PATENT DOCUMENTS

| | | | |
|---|---|---|---|
| 9,760,702 B1 * | 9/2017 | Kursun | G06Q 20/4016 |
| 10,286,917 B2 * | 5/2019 | Olsen | B60R 16/037 |
| 2014/0078407 A1 | 3/2014 | Green | |
| 2016/0129916 A1 | 5/2016 | Olsen | |
| 2017/0175411 A1 | 6/2017 | Bowers | |

* cited by examiner

INFORMATION AND PASSIVE BIOMETRIC SYSTEMS AND METHODS

CROSS-REFERENCE TO RELATED APPLICATION

This application claims priority to and benefit of U.S. Provisional Patent Application No. 62/578,892, filed Oct. 30, 2017, which is hereby incorporated by reference herein in its entirety.

TECHNICAL FIELD

This disclosure relates to information and passive biometric systems and more specifically to an information system having a transparent or translucent graphical user interface and a transparent or translucent input interface that selectively reveals or obscures tangible items behind the interfaces, and to a system of biometric sensors used to passively identify and differentiate among different humans moving about a space.

BACKGROUND

As people age, many move into retirement communities, assisted living facilities, and/or nursing homes for a variety of reasons. For example, some retired/elderly people (e.g., 70+ years old, 80+ years old, 90+ years old, etc.) need extra help with daily activities/tasks like food preparation, bathing, cleaning, etc. Other retired/elderly people simply like the convenience of having their doctor on-site and/or medical staff that is in-house and trained to aid medically in a prompt manner when needed. Prior systems exist to alert medical staff of a need for medical help; however, these prior systems typically require the person to press a button on a remote or pull a chain on the wall. Further, privacy concerns militate against installing imaging cameras and/or audio recording device in the residences of these residents. Thus, a need exists for a system that maintains the privacy of the residents/patients, but does not rely on the resident/patient having to manually activate an alarm when medical help is needed. The present disclosure is directed to solving these problems and addressing other needs.

Retired and elderly people enjoy privacy and feelings of independence that erode as they need to lean on other humans for help with daily activities, which can be intrusive in their personal space and decrease dignity. However, it is also important for the living facility operator to ensure the safety of the residents, and part of this responsibility includes having visibility on the location, well-being, and activities of each resident, in the most non-intrusive and dignified manner possible. Personalization is important to maintaining each resident's self-identity and making the resident's room within a broader living facility to bear reminders of the home and people the resident is now be separated from. When a resident needs help, the living facility staff charged with their care need to be able to react promptly and meaningfully, which involves knowing where the resident is physically when an alarm or alert is raised, and information about what may have triggered the alarm or alert so that the first responder can be prepared to render the correct type of aid or assistance. Eventually, residents may fall into a routine, so it is also important to understand those routines and learn each resident's behavior so that outlier activities that deviate from established routines and behavior can be flagged and raised to the caregivers in the facility for possible action. Machines, including computers, can aid in learning routines and behavior and movement patterns of each resident, but again, to maintain dignity, privacy, and feelings of independence, such learning routines should be as non-intrusive and invisible to the residents as possible, without relying on active tracking of each resident or requiring the residents to wear or carry any active tracking devices. The present disclosure is to solving these problems and addressing other needs.

BRIEF SUMMARY

Motion sensors and LED lighting are installed around various rooms of a residence, for example, by being embedded or incorporated into furniture or as standalone plug-and-play units that can be plugged into a power supply outlet. The lighting is installed so that it illuminates the floor, creating a soft, uniform glow effect on the floor that is not blinding or shocking to dilated pupils. At nighttime, when the resident gets out of bed, for example, the motion sensors and lights are activated together or in sequence to create a lighted pathway for the resident from the bed to another room, such as the bathroom or kitchen, which is typically where the resident heads at nighttime. The movement patterns of the resident are captured and stored to make intelligent autonomous decisions about whether to raise an alert and/or an alarm with a central monitoring station, such as one typically manned by a nursing station. Different light colors can be used to indicate an alarm condition so that nurses can use the light as a visual confirmation that they have entered the correct residence, or to indicate that certain events have or need to occur, such as dispensation or taking of medication (e.g., green light indicates time to take medicine, red light indicates an alarm was triggered, orange indicates an alarm is about to be triggered if an action is not taken by the resident, etc.). Alerts can be sent when the resident reaches the bathroom, and an alarm can be communicated wirelessly when the algorithm determines that an anomalous amount of time has been spent in the bathroom without detecting a movement out of the bathroom and/or within the bathroom. The lighting can be turned red as the alarm is raised, so that when a caregiver enters the room, the red lighting immediately indicates as a visual signal that the caregiver is in the room that raised the alarm. The system is modular and expandable, and readily retrofittable into an existing residence without requiring invasive inconvenience to the resident who may already be living in the residence. Power consumption is also an issue with conventional systems, so the present disclosure exploits the tendency to arrange furniture near wall outlets to incorporate the lighting and sensors into the furniture so that the power and data cables can be concealed within the furniture and can be plugged directly into a wall outlet that the furniture tends to be located nearby, without creating tripping hazards to the resident. In residences where a lighting and sensor module is needed in a zone where there are no furniture items nearby to conceal the module items, aspects of the present disclosure provide a plug-and-play module having integrated sensors and lights that plugs directly into a wall outlet and communicates wirelessly with a central hub and/or station to relay sensor outputs and receive lighting commands. The alerts and alarms generated by aspects of the present system can be used to augment or supplement an existing alerting and alarming system already installed in an assisted living care facility. It creates a feeling of independence or autonomy for the resident with additional peace of mind for loved ones outside the residence and caregivers who are responsible for the immediate wellbeing and welfare of the resident.

To track movement, the sensor system logs when a sensor is triggered (e.g., a timestamp) and which one. Each sensor output can be wirelessly communicated to a central controller or to another sensor assembly in a relay or daisy-chain manner. A unique device ID differentiates which sensor was triggered, and a timestamp applied to each output provides the central controller with a map or direction of travel that can be determined from the timestamps and device IDs. An alert can be sent to a nursing station, for example, when a particular sensor is triggered, thereby indicating that the resident has reached, for example, the bathroom. An alarm can be generated if the resident does not return from the bathroom within a predetermined time period or a time period that is learned over time to be an anomalous amount of time compared to previous bathroom visits. Typically, the residents have multiple alarm systems that can be deployed by the resident, such as a pull cord alarm near the toilet or a portable alarm worn around the neck with a button that is pressed to raise an alarm. If neither of these alarms is raised by the resident, the system can operate as a failsafe or backup to trigger an alarm autonomously and automatically if the resident becomes unable to manually trigger an alarm by pulling a cord or pressing a button on a portable alarm. However, if the resident returns to bed within an expected period of time, the system tracks and timestamps the movement of the resident from the bathroom back to bed by determining from the device IDs and timestamps that the resident has triggered all expected sensors in the expected time period along a path that indicates a direction of travel from the bathroom back to the bed. All of these activities are recorded, and can be used by a machine learning algorithm to determine movement patterns to help the machine determine when to raise an alarm based on outlier activities.

To make the system as innocuous to the resident as possible, the sensors can be integrated into furniture in a way that would not reveal their presence. For example, a PIR sensor requires an unimpeded window that is transparent to infrared energy to be able to sense heat. This means that the PIR sensor cannot be completely concealed, because wood is not necessarily transparent to infrared energy. However, according to some aspects disclosed herein, the PIR sensor can be incorporated into a handle or knob of a furniture item, and the transparent window can be opaque and colored to match the color of the knob or furniture. The lighting can be an LED strip that is mounted above, for example, a toe kick plate so that the lights illuminate the floor near the kick plate in a downwardly manner, creating a soft glow on the floor in front of the furniture item. The overall visual effect is a lighted pathway on the floor created by the LED strips mounted on the furniture throughout the residence so that the resident is not blinded by bright light and can use the lighted pathway as a visual aid to move safely from the bed to the bathroom or other destination in the residence.

It is common for residents living in an assisted living facility to have their own personal private space, such as an apartment or bedroom. Outside of the entrance door to apartment or room is installed an apparatus herein called a memory box. A memory box stores tangible items of personal meaning to the resident, such as personal mementos, keepsakes, and other items of sentimental value or significance to the resident, to personalize and differentiate the resident's entrance and to identify items of personal importance to the resident. The memory box is partly or completely covered by a transparent or translucent video display having an overlaying touch-sensitive interface, which is also transparent or translucent. When the display is black, the tangible items in the memory box become visible through the transparent display. When the display is on, photographs can be displayed in a slideshow pattern on the display, which obscures the tangible items and renders them opaque to the viewer. When the resident inside the apartment or room activates a pendant (such as worn around the neck) or a fixed pull cord (such as installed near a toilet) alarm, a corresponding signal is communicated to a remote server, which in turn sends a command wirelessly to the memory box to change its display to portraying an alarm condition, such as by flashing or pulsing a bright solid red color or by displaying some similar indicia of an alarm. The tangible items inside the box become obscured and are rendered opaque to the viewer. When an alarm is triggered that affects the entire building, such as a fire alarm, every resident's memory box can be made to flash (e.g., during a bad weather warning) or to show arrows of direction of travel (e.g., when a fire or smoke alarm is triggered) to facilitate an orderly evacuation of the facility. Finally, the memory box can also be used as an input interface to log check-ins and check-outs of caregivers entering and leaving the resident's room. The touch-sensitive interface can receive inputs made relative to a keypad displayed on the display, such as a unique PIN identified to each caregiver, who inputs the PIN each time the caregiver enters and leaves a resident's room. Timestamps of these activities are communicated wirelessly from the memory box to the remote server for logging. Whether the display is transparent or opaque can also indicate whether the resident is inside the room or not. Alternately, a separate indicia can be displayed on the display to indicate that the resident is inside or not inside the room. For example, if the personal momentos and other tangible items can be seen in the memory box, this could indicate that the resident is not inside the room. However, if the digital photographs are being displayed and cycled on the memory box, this could indicate that the resident is inside the room.

To track a resident's movements anywhere within a space, a system of passive biometric sensors is also contemplated. A unique signature based on resident's weight and a resident's particular seating position can be used to uniquely identify a resident. For example, starting in the resident's bed inside their room, weight sensors can determine the resident's weight. Because the same resident sleeps in the same bed each night, weight is the only biometric that needs to be obtained from the bed. When a resident leaves the room and enters a common living space, furniture is typically arranged about the space for any resident to use. Thus, chairs have arrays of pressure sensors embedded in their seats, backs, and optionally armrests, which create a unique pattern for each resident who sits in the chair. Using the weight information obtained from the bed, and the pressure pattern, the system can differentiate one resident from another. Residents tend to become creatures of habit, preferring to sit in the same chair over time, which helps to form a baseline for each resident and to identify outliers and anomalies that deviate from the baseline. Dining room chairs, lounge chairs, recliners, sofas, and other seating furniture can have similar pressure sensors arrays embedded in a hidden manner beneath the surfaces that come into contact with the resident. Likewise, mats can be placed on the floor of a space, e.g., near a door to exit a facility, with pressure or weight sensors to determine the weight and/or pressure pattern of a person who stands on the mat. Thus, when a resident enters or leaves the facility, they can be identified based on a comparison of the weight determined from stepping or standing on the mat against the weight determined from their bed sensors. Because residents in a living facility spend the majority of their time in a prone or sitting position, they can be tracked using this system of passive biometric sensors, and their movement and behavior routines mapped and logged for baselining, diagnostic, and tracking purposes. These sensor systems can also differentiate whether the resident is standing, sitting, or sleeping, and these statuses can be communicated to other monitoring systems to begin monitoring for anomalies. Direction of movement sensors can also be placed around a space, such as being embedded into furniture or nightlights, to track movement directions of residents from one furniture item to another or from one room to another.

According to some implementations of the present disclosure, a method of illuminating a path in a location for a human includes receiving, from a first motion sensor, a first signal indicating detection of movement of the human in a first predefined zone in the location. Responsive to the receiving the first signal, log data is generated that is indicative of the movement of the human detected in the first predefined zone and a time that the movement of the human was detected. A second signal indicating an amount of ambient light in the first predefined zone is received, from a first ambient light sensor. Responsive to (i) the indicated amount of ambient light being below a threshold and (ii) the received the first signal, an activation signal is communicated to cause a first light source that is incorporated into or on an item of furniture in the first predefined zone to be activated such that the first light source provides downward illumination of a floor area in at least a portion of the first predefined zone.

According to some implementations of the present disclosure, a method includes receiving, from a first motion sensor, a first signal indicating detection of a first movement of a human in a first predefined zone in a location at a first time. Responsive to the receiving the first signal, (i) a first activation signal is communicated to cause a first light source that is incorporated into or on a first item of furniture in the first predefined zone to be activated such that the first light source provides downward illumination of a first floor area in at least a portion of the first predefined zone and (ii) a second activation signal is communicated to cause a second light source that is incorporated into or on a second item of furniture in a second predefined zone, that is separate and distinct from the first predefined zone, to be activated such that the second light source provides downward illumination of a second floor area in at least a portion of the second predefined zone. Responsive to an absence of receiving, from the first motion sensor, a second signal indicating detection of a second movement of the human in the first predefined zone in the location at or before a second time that is after the first time, an alarm signal is transmitted.

According to some implementations of the present disclosure, a method of illuminating a path in a location for a human includes receiving, from a first motion sensor, a first motion signal indicating detection of a first movement of the human in a first predefined zone in the location at a first time. Responsive to the receiving the first motion signal: a first alert signal is communicated and log data is generated that is indicative of the first movement of the human detected in the first predefined zone and the first time. An ambient light signal is received from a first ambient light sensor that indicates an amount of ambient light in the first predefined zone. Responsive to (i) the indicated amount of ambient light in the first predefined zone being below a threshold and (ii) the receiving the first motion signal: a first activation signal is communicated to cause a first light source that is incorporated into or on a first item of furniture in the first predefined zone to be activated such that the first light source provides downward illumination of a first floor area in at least a portion of the first predefined zone, and a second activation signal is communicated to cause a second light source that is incorporated into or on a second item of furniture in a second predefined zone, that is separate and distinct from the first predefined zone, to be activated such that the second light source provides downward illumination of a second floor area in at least a portion of the second predefined zone. Responsive to receiving, from the first motion sensor, a second motion signal indicating detection of a second movement of the human in the first predefined zone in the location at or before a second time that is after the first time, a second alert signal is transmitted. Responsive to an absence of receiving, from the first motion sensor, the second motion signal indicating detection of the second movement of the human in the first predefined zone in the location at or before the second time, an alarm signal is transmitted.

According to some implementations of the present disclosure, a method of illuminating a path in a location for a human includes receiving, from a first motion sensor, a first motion signal indicating detection of a first movement of the human in a first predefined zone in the location at a first time. Responsive to the receiving the first motion signal, log data is generated that is indicative of the first movement of the human detected in the first predefined zone and the first time. A first ambient light signal is received from a first ambient light sensor indicating an amount of ambient light in the first predefined zone. Responsive to (i) the indicated amount of ambient light in the first predefined zone being below a threshold and (ii) the receiving the first motion signal, a first activation signal is communicated to cause a first light source that is incorporated into or on a first item of furniture in the first predefined zone to be activated such that the first light source provides downward illumination of a first floor area in at least a portion of the first predefined zone. A second motion signal is received from a second motion sensor indicating detection of a second movement of the human in a second predefined zone in the location at a second time that is after the first time. Responsive to the receiving the second motion signal, log data is generated that is indicative of the second movement of the human detected in the second predefined zone and the second time. A second ambient light signal is received from a second ambient light sensor indicating an amount of ambient light in the second predefined zone. Responsive to (i) the indicated amount of ambient light in the second predefined zone being below the threshold and (ii) the receiving the second motion signal: a second activation signal is communicated to cause a second light source that is incorporated into or on a second item of furniture in a second predefined zone, that is separate and distinct from the first predefined zone, to be activated such that the second light source provides downward illumination of a second floor area in at least a portion of the second predefined zone. A deactivation signal is communicated to cause the first light source to be deactivated.

According to some implementations of the present disclosure, a system for use in illuminating a path in a location includes a first motion sensor, a first ambient light sensor, a first light source, and a master controller. The first motion sensor is incorporated into or on a first item of furniture in a first predefined zone in the location. The first ambient light sensor is incorporated into or on the first item of furniture or a second item of furniture in the first predefined zone. The first light source is incorporated into or on the first item of furniture, the second item of furniture, or a third item of furniture in the first predefined zone. The master controller includes one or more processors and a memory device storing instructions that when executed by at least one of the one or more processors cause the system to: receive in the master controller from the first motion sensor a first motion signal indicating a detection of a first movement of a human in the first predefined zone in the location. Log data is generated in the master controller that is indicative of the first movement of the human and a time that the first movement of the human was detected. An ambient light signal is received in the master controller from the first ambient light sensor that indicates a measured amount of ambient light in at least a portion of the first predefined zone. A determination is made in the master controller if the measured amount of ambient light is less than a threshold amount of ambient light. Responsive to (i) a determination that the measured amount of ambient light is less than the threshold and (ii) the received first motion signal, an activation signal is transmitted, from the master controller to the first light source, to cause the first light source to provide downward illumination of a first floor area in at least a portion of the first predefined zone.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

Figure 1:
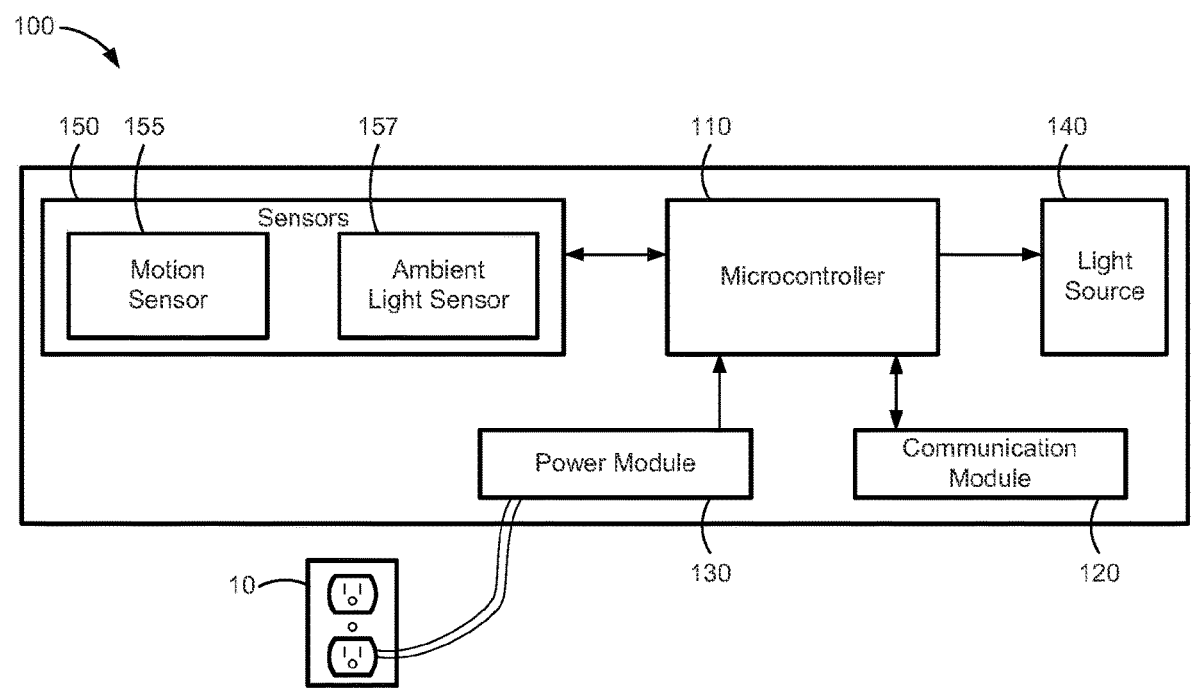
FIG. 1 is a schematic block diagram of a motion-activated lighting unit according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Referring to FIG. 1, a motion-activated lighting unit 100 includes a microcontroller 110, a communications module 120, a power module 130, a light source 140, and sensors 150. The components of the motion-activated lighting unit 100 can be housed in one or more housings. In some implementations, all of the components are housed in a single housing.

In some other implementations, the microcontroller 110, the communications module 120, and the power module 130 are housed in a first housing, the light source 140 is housed in a second housing that is separate and distinct from the first housing, and the sensors 150 are housed in a third housing that is separate and distinct from the first housing and the second housing. In some such implementations, the components in the first, second, and third housings can be connected via one or more wires (e.g., data and/or power wires) extending between the housings and/or wirelessly. For example, the light source 140 in the second housing can be connected to the microcontroller 110 in the first housing via a cable capable of transmitting power and/or data in a wired fashion. Alternatively, the light source 140 in the second housing can be connected to the microcontroller 110 in the first housing in a wireless manner. Similarly, the sensors 150 in the third housing can be connected to the microcontroller 110 in the first housing via a cable capable of transmitting power and/or data in a wired fashion. Alternatively, the sensors 150 in the third housing can be connected to the microcontroller 110 in the first housing in a wireless manner.

In yet a further implementation, the microcontroller 110, the communications module 120, and the power module 130 are housed in a first housing, and the light source 140 and the sensors 150 are housed in a second housing that is separate and distinct from the first housing. Various other arrangements/groupings of the components of the motion-activated lighting unit 100 are contemplated (e.g., all components can have their own separate and distinct housing).

The microcontroller 110 can include any number and any type of controllers and/or processors and/or memory devices capable of controlling operation of the motion-activated lighting unit 100. For example, the microcontroller 110 can include one or more processors and a memory device storing instructions that when executed by at least one of the one or more processors cause the motion-activated lighting unit 100 to perform or conduct one or more actions (e.g., cause the light source 140 to turn on or off, detect motion of a human, determine an amount of ambient light, transmit an alert signal and/or an alarm signal, etc., or any combination thereof as described further herein).

The communications module 120 can be any type of communications module capable of wired and/or wireless communications with external units (e.g., other motion-activated lighting units, either directly or indirectly) and/or servers (e.g., remote servers, local servers, etc.) and/or controllers (local master controllers, remote master controllers, controllers in other motion-activated lighting units, etc.). The communications module 120 is coupled to the microcontroller 110 such that the microcontroller 110 can cause the communications module 120 to transmit one or more alerts/notifications, alarms/warnings, instructions, etc. to one or more third parties (e.g., a nursing station, an emergency medical provider, 911, a hospital, a doctor, one or more designated family members, etc. as described further herein).

The motion-activated lighting unit 100 is shown as being powered via the power module 130 being plugged in (e.g., wired) to a standard 120/240V wall electrical outlet 10. Alternatively, the motion-activated lighting unit 100 can include one or more batteries to power one or more of its components. As shown in FIG. 1, the microcontroller 110 is coupled to all of the other components of the motion-activated lighting unit 100 to transmit power from the power module 130. Alternatively, one or more of the components of the motion-activated lighting unit 100 can be directly connected to the power module 130 to receive power therefrom and/or be directly connected to the electrical outlet 10. For example, in some alternative implementations, the light source 140 can be directly plugged into the electrical outlet 10 to receive its power therefrom.

The light source 140 can include any number of lights/bulbs/LED modules, etc. (e.g., one light, two lights, five lights, twenty lights, fifty lights, etc.) and any type of lights (e.g., LED, incandescent, etc.). The light source 140 is coupled to the microcontroller 110 such that the microcontroller 110 can cause the light source 140 to turn on and off based on the occurrence of one or more events (e.g., in response to the detection of motion of a human in a predefined zone in a location). The light source 140 can emit one or more colors of light in an emission range of the light source 140, which can depend on the orientation/direction of the light source 140. For example, the light source 140 can emit white light, soft white light, daylight, yellow light, blue light, red light, green light, orange light, etc. The color of the emitted light can depend on a variety of factors described further herein.

The sensors 150 include a motion sensor 155 that is able to detect motion of, for example, a human moving within a defined sensing range of the motion sensor 155. The motion sensor 155 can be any type of motion sensor, such as, for example, a passive infrared motion sensor (PIR sensor), etc. that detects infrared radiation emitted by the human. The PIR sensor can include one or more Fresnel lenses to improve the range of the motion sensor. In the case of the motion sensor 155 being a PIR sensor, the motion sensor 155 is only capable of detecting motion by a change in infrared radiation/light detected (i.e., a change in heat in the sensing range of the motion sensor caused by a human moving past the motion sensor 155) and does not capture images or sound of the human(s) interacting with the motion sensor 155. As such, the motion sensor 155 of the present disclosure is able to provide a level of privacy not afforded by some other sensors used to detect and/or capture motion data (e.g., video cameras, still cameras, etc.). A window that is transparent to infrared energy can be opaque and preferably have a color that blends with or matches a color of the furniture item in which the motion sensor 155 is installed or integrated. In some aspects, the window has a diameter or width that does not exceed about half an inch. As mentioned above, the window can optionally include facets forming a Fresnel lens to expand the detection range of the motion sensor 155.

The sensors 150 can include one or two or more motion sensors 155. In some such implementations, two or more motion sensors 155 can be positioned in a known relationship relative to each other for use in determining a direction of movement/travel of a human (e.g., moving left to right or right to left or standing up to sitting down or vice versa).

The sensors 150 also include an ambient light sensor 157 that is configured to detect an amount of ambient light in, for example, a predefined zone of interest. In some implementations, the ambient light sensor 157 and the motion sensor 155 are the same sensor capable of sensing both motion and ambient light. In some other implementations, the ambient light sensor 157 and the motion sensor 155 are two separate and distinct sensors that are housed in either the same housing or two separate and distinct housings. The ambient light sensor 157 is placed where non-natural light cannot create false readings by the ambient light sensor 157. The ambient light sensor 157 is for detecting a dark room. In some aspects, a clock can also be used to determine the time of day to minimize false readings.

Figure 2:
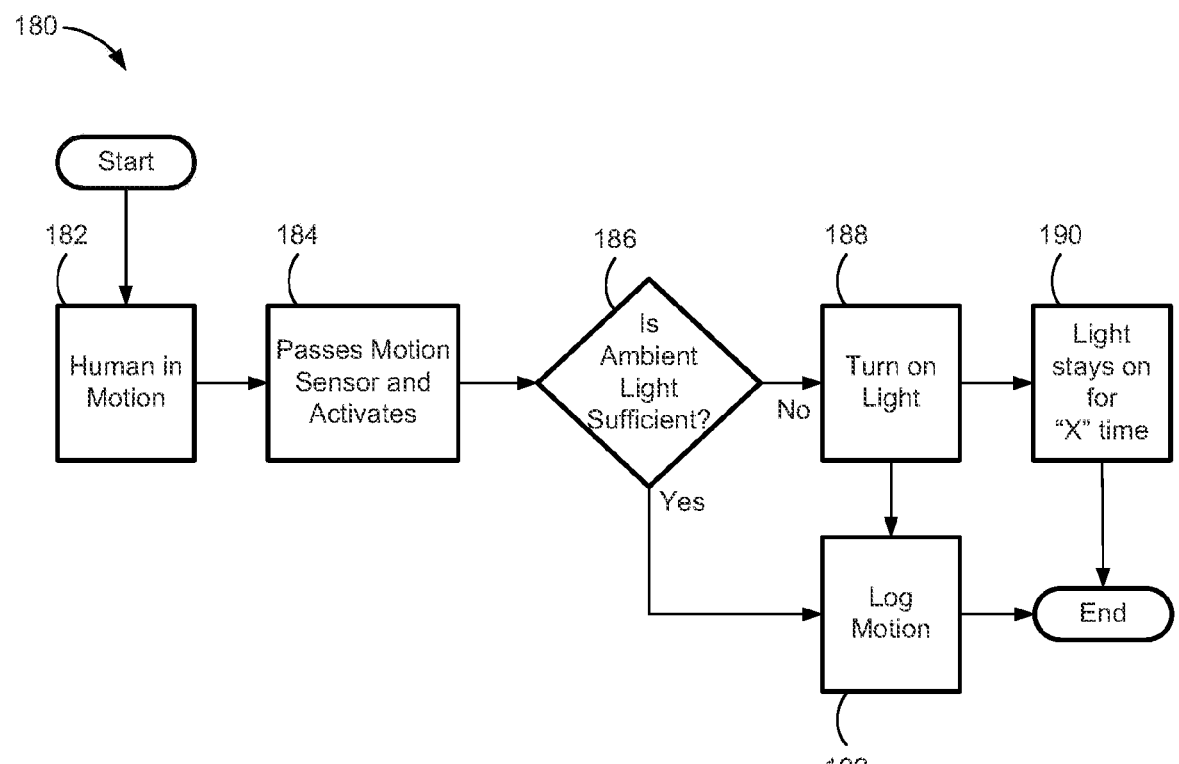
FIG. 2 is a flow chart illustrating a method of operating the motion-activated lighting unit of FIG. 1 according to some implementations of the present disclosure.

Referring to FIG. 2, a method 180 of operating the motion-activated lighting unit 100 is described. The method starts with motion of a human 182 in a location (e.g., an apartment, a hospital room, a room or zone or area in a nursing home/hospital, a room in an assisted living facility, etc.). Next, the human enters or moves into a sensing range of the motion sensor 155, which defines a predefined zone of the location that is being monitored by the motion-activated lighting unit 100. This causes the motion sensor 155 to detect motion 184, for example, by detecting/sensing/determining/calculating a heat signature of the human moving within and/or across the sensing range of the motion sensor 155.

After the motion is detected/sensed/determined/calculated, the ambient lighting can be checked by the ambient light sensor 157 to determine if the ambient light is sufficient 186. By sufficient ambient light it is meant that the amount of measured ambient light exceeds a threshold value (e.g., the threshold value can be about five lumens per square foot, about ten lumens per square foot, about fifteen lumens per square foot, about twenty lumens per square foot, etc. or any number in-between). When the amount of ambient light measures below the threshold value, that is an indication that the ambient light is not sufficient (e.g., the ambient light is not enough for a human to readily see the floor when walking). If the amount of ambient light is determined to not be sufficient (e.g., the microcontroller 110 receives the measured amount of ambient light from the ambient light sensor 157 and determines that the measured amount is below the threshold), then the light source 140 is turned on 188 (e.g., by the microcontroller 110) and stays on for an amount of time 190.

The amount of time that the light source 140 stays on can depend on a variety of factors and/or just be a preset amount of time (e.g., ten seconds, thirty seconds, one minute, five minutes, thirty minutes, etc.). In some implementations, the light source 140 stays on until a second or subsequent motion is sensed by the motion sensor 155, which can indicate a return of the human. In some other implementations, the light source stays on until a second motion is sensed by a different motion-activated lighting unit that is communicatively coupled to the motion-activated lighting unit 100 including the motion sensor 155. In some such implementations, the detected second motion can indicate that the human moved from the sensing range of the motion sensor 155 and thus, the light of the light source 140 is no longer needed to be on.

Even if the amount of ambient light is determined to be sufficient (i.e., the light source 140 is not needed to be on), log data is generated 192 (e.g., by the microcontroller 110) that is indicative of the detected motion. Further, in response to the light being turned on, log data is also generated 192 (e.g., by the microcontroller 110) that is indicative of the detected motion. In some implementations, additional data is also generated with the log data, such as, for example, a time stamp associated with the time that the motion was detected (e.g., 1:08 AM), a direction of travel of the human, etc., or any combination thereof.

Such log data and additional data can be used to develop movement patterns of one or more humans interfacing with the motion-activated lighting unit 100. For example, a movement pattern of a human might be that between 12:30 AM and 1:00 AM most nights, the human gets out of bed, walks to the bathroom, spends about five minutes in the bathroom using the toilet, and then returns to bed. As described herein, use of a multitude of the motion-activated lighting units 100 can facilitate a method of illuminating a path with lights for a human moving through a location at times having low and/or insufficient ambient light.

Figure 3:
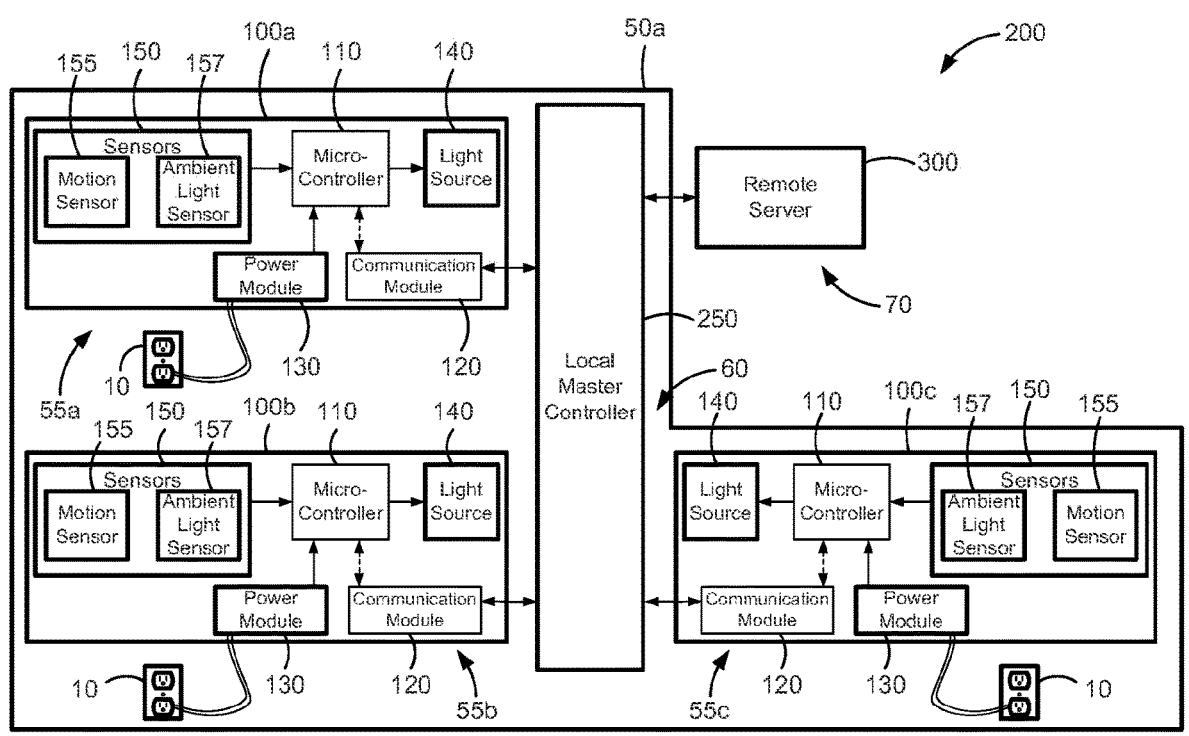
FIG. 3 is a schematic block diagram of a motion-activated lighting system in a location according to some implementations of the present disclosure.

Referring to FIG. 3, a motion-activated lighting system 200 includes a first motion-activated lighting unit 100a, a second motion-activated lighting unit 100b, a third motion-activated lighting unit 100c, a local master controller 250, and a remote server 300. Each of the first, second, and third motion-activated lighting units 100a, 100b, and 100c are the same as, or similar to, the motion-activated lighting unit 100 described above in connection with FIGS. 1 and 2, where like reference numbers are used for like components.

As shown, the first motion-activated lighting unit 100a is positioned in a first predefined zone or area 55a of the location 50a, the second motion-activated lighting unit 100b is positioned in a second predefined zone or area 55b of the location 50a, and the third motion-activated lighting unit 100c is positioned in a third predefined zone or area 55c of the location 50a. The first, second, and third predefined zones 55a, 55b, 55c can be any room or portion of a room in the location 50a. For example, the first predefined zone 55a can be a bedroom or an area next to a first side of the bed adjacent to a first night stand, the second predefined zone 55b can be an area next to a second side of the bed adjacent to a second night stand, and the third predefined zone 55c can be a bathroom or an area next to a toilet in the bathroom. As shown, each of the first, second, and third predefined zones 55a, 55b, 55c is a separate and distinct zone with no overlap therebetween. Alternatively, one or more of the predefined zones can overlap with one another.

Each of the first, second, and third motion-activated lighting units 100a, 100b, and 100c is communicatively coupled to the local master controller 250 in a wired and/or wireless manner. As shown, the local master controller 250 is positioned in a fourth predefined zone or area 60 of the location 50a. The fourth predefined area 60 can be any room or portion of a room in the location 50a, such as, for example, a closet, a cabinet, a shelf, etc. In some implementations, the local master controller 250 and the first, second, and third motion-activated lighting units 100a, 100b, and 100c are configured to work in a hub and spoke relationship where each of the first, second, and third motion-activated lighting units 100a, 100b, and 100c only communicates with the local master controller 250 and the local master controller 250 communicates with any of the first, second, and third motion-activated lighting units 100a, 100b, and 100c. Alternatively, each of the first, second, and third motion-activated lighting units 100a, 100b, and 100c can directly communicate with one another (e.g., without using/going through the local master controller 250).

The remote server 300 is positioned in a fifth predefined zone or area 70 that is remote from (i.e., not within) the location 50a. The fifth predefined area 70 can be any area that is remote from (i.e., outside of) the location 50a. For example, the fifth predefined area 70 can be a nursing station in a building including the location 50a and the nursing station, a closet, a cabinet, a shelf, a desk, etc.

The local master controller 250 and the remote server 300 are communicatively coupled in a wired and/or wireless fashion such that communications and/or data can be readily transmitted therebetween. For example, the local master controller 250 is able to transmit/send one or more alerts/notifications, alarms/warnings, instructions, etc. to the remote server 300 such that a third party monitoring the remote server 300 can receive and view the transmission and take any necessary actions based on the received transmission. For example, in response to receiving a motion signal (e.g., from one of the third motion-activated lighting unit 100c), the local master controller 250 may transmit an alert signal to the remote server 300 (wirelessly and/or in a wired fashion) indicating that motion was detected by the third motion-activated lighting unit 100c located in the third predefined zone or area 55c of the location 50a (e.g., the bathroom). In some such implementations, the alert signal may contain information and/or be indicative of information that the human residing in the location 50a is out of bed, is in the bathroom, is in the kitchen, left the location 50a, any combination thereof, etc.

For another example, the local master controller 250 may transmit an alarm signal to the remote server 300 indicating that a return motion (e.g., a second or subsequent motion signal) was not detected by the first motion-activated lighting unit 100a located in the first predefined zone or area 55a of the location 50a (e.g., the bedroom), which may indicate that the human being monitored is experiencing a potential non-normal behavior. For example, while there are many reasons why a human may leave their bed at 1 AM and not return within a predetermined amount of time (e.g., ten minutes), the non-detection of a return motion at the first predefined zone (e.g., the bedroom or the first predefined zone to detect motion in the given period being considered/monitored) can indicate that the human fell and/or collapsed etc. while using the bathroom or getting a drink in the kitchen and needs assistance.

While only three motion-activated lighting units 100 are shown in the location 50a, any number of motion-activated lighting units 100 can be included in the location 50a (e.g., one motion-activated lighting unit 100, five motion-activated lighting units 100, ten motion-activated lighting units 100, one hundred motion-activated lighting units 100, etc.). Each of the motion-activated lighting units 100 in the location 50a can be strategically positioned to monitor/cover specific areas of the location 50a. In some implementations, the monitored areas are separate and distinct (i.e., no overlap in coverage) and in other implementations, some or all of the monitored areas of the motion-activated lighting units 100 at least partially overlap. By overlap it is meant that the sensing range of the motion sensors 155 of each of the motion-activated lighting units 100 cross into the sensing range of one or more adjacent motion-activated lighting units 100. Alternatively or additionally, by overlap it is meant that the range of the light source 140 of each of the motion-activated lighting units 100 crosses into the range of the light source 140 of one or more adjacent motion-activated lighting units 100.

Figure 4:
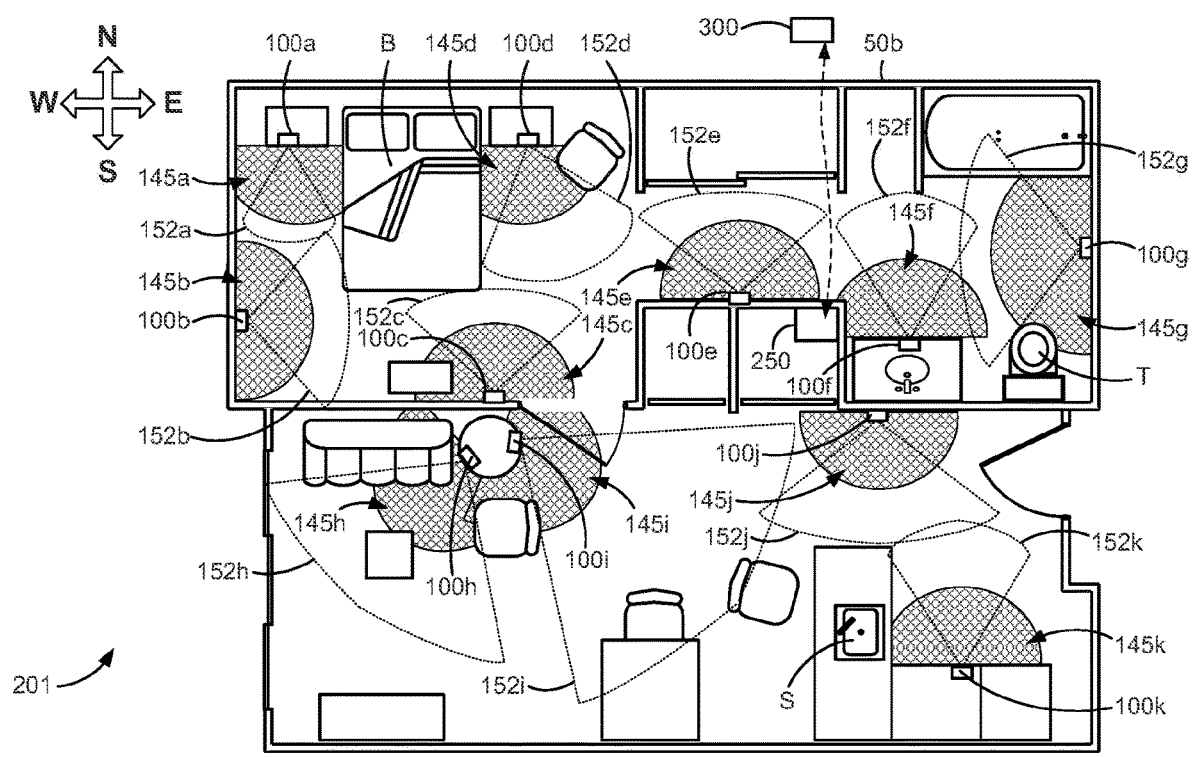
FIG. 4 is a plan schematic illustration of a motion-activated lighting system in a location according to some implementations of the present disclosure.

Referring to FIG. 4, a motion-activated lighting system 201 includes the local master controller 250, the remote server 300, and eleven of the motion-activated lighting units 100, which are labeled 100a-100k. Each of the motion-activated lighting units 100a-100k is the same as, or similar to, the motion-activated lighting unit 100 described above in connection with FIGS. 1 and 2, where like reference numbers are used for like components.

As shown, the motion-activated lighting units 100a-100k are strategically positioned throughout the location 50b for use in (i) detecting motion of one or more humans/patients/residents in the location 50b, (ii) determining an amount of ambient lighting in select areas of the locations 50b, via the ambient light sensor 157 in each of the motion-activated lighting units 100a-100k, and (iii) intelligently illuminating select areas of the location 50b, via the light sources 140 in each of the motion-activated lighting units 100a-100k being turned on and off. The location 50b is an apartment or residence of one or more humans/patients/residents and includes, for example, a number of furniture items (e.g., nightstands, dressers, desks, cabinets, etc.), a bed, B, a toilet, T, a sink, S, closets, chairs, a couch, tables, etc., among other items as illustrated. The location 50b is only illustrative and can have any number or type of items therein, and can have any orientation or arrangement.

Further, each of the motion-activated lighting units 100a-100k has an illumination range 145a-145k, respectively, (illustrated by line hatching) of its light source 140 and a sensing range 152a-152k, respectively, (illustrated by dotted lines) of its motion sensor 155. For example, the light source 140 of the first motion-activated lighting unit 100a has an illumination range 145a and the motion sensor 155 of the first motion-activated lighting unit 100a has a sensing range 152a. Similarly, the light source 140 of the eleventh motion-activated lighting unit 100k has an illumination range 145k and the motion sensor 155 of the eleventh motion-activated lighting unit 100k has a sensing range 152k. In some implementations, each of the sensing ranges 152a-152k of the motion-activated lighting units 100a-100k defines a predefined zone of the motion-activated lighting system 201 within the location 50b. The predefined zones of the motion-activated lighting system 201 can be separate and distinct zones (i.e., no overlap between adjacent predefined zones) and/or one or more of the predefined zones can overlap at least partially with one or more adjacent predefined zones of the motion-activated lighting system 201. In some such implementations where the predefined zones are separate and distinct (i.e., no overlap), the motion sensor 155 of a first one of the motion-activated lighting units 100a-100k cannot detect/sense/determine motion occurring in any of the other predefined zones.

Each of the motion-activated lighting units 100a-100k is communicatively coupled to the local master controller 250 in a wireless fashion such that each of the motion-activated lighting units 100a-100k is able to send and/or receive data and/or instructions to/from the local master controller 250. For example, in some implementations, responsive to one of the motion-activated lighting units 100a-100k sensing motion of a human within its sensing range 152a-k, the one of the motion-activated lighting units 100a-100k wirelessly transmits data to the local master controller 250 indicative of the sensed motion. For another example, in some implementations, responsive to one of the motion-activated lighting units 100a-100k measuring an amount of ambient light, the one of the motion-activated lighting units 100a-100k wirelessly transmits data to the local master controller 250 indicative of the measured amount of ambient light.

For yet another example, in some implementations, responsive to the local master controller 250 receiving data indicative of motion of a human occurring in a first predefined zone (e.g., the sensing range 152a of the first motion-activated lighting unit 100a), the local master controller 250 transmits, wirelessly, data and/or instructions to one or more of the motion-activated lighting units 100a-100k instructing the microcontroller 110 to turn on the light source 140. In some such implementations, the transmitted instructions are only to the first motion-activated lighting unit 100a (i.e., the unit where the motion was detected). In some other such implementations, the transmitted instructions are to the first motion-activated lighting unit 100a (i.e., the unit where the motion was detected) and to the second motion-activated lighting unit 100b (i.e., the unit next in the walking path or the unit directly adjacent to the unit 100a where the motion was detected). Further, in some other such implementations, the transmitted instructions are to all of the motion-activated lighting units that are in a predetermined walking path of the human based on a variety of factors (e.g., time of the day/night, a library of known or learned movement patterns for the human, which one of the motion-activated lighting units 100a-100k was the first to sense motion, etc.).

In some implementations, the sensors 150 in each of the motion-activated lighting units 100a-100k include one or more motion sensors 155 in a known relationship relative to each other for use in determining a direction of movement/travel of a human (e.g., moving left to right or right to left). For example, the relative positioning of each of the motion-activated lighting units 100a-100k and/or the relative positioning of the one or more motion sensors 155 in each of the motion-activated lighting units 100a-100k can be stored in a relationship database for use in determining direction of travel of the human within the motion-activated lighting system 201.

Figure 5A:
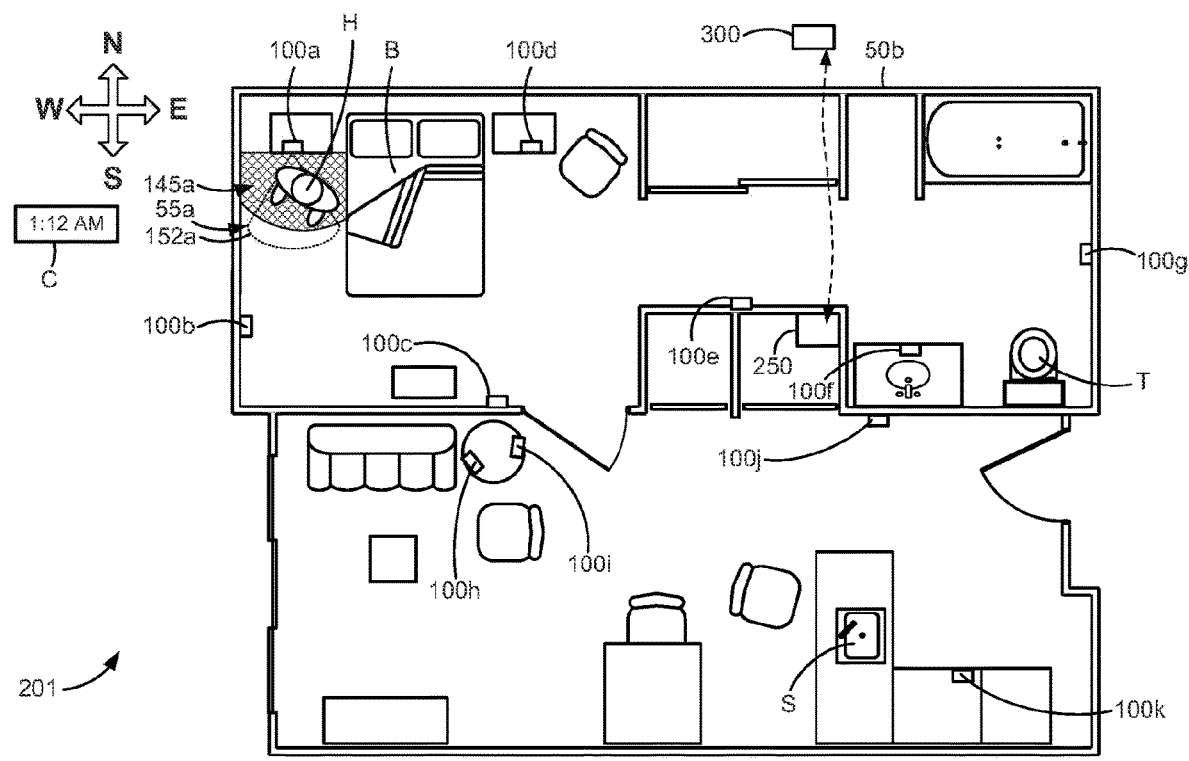
FIG. 5A is a plan schematic illustration of the motion-activated lighting system of FIG. 4 illustrating a first stage of an intelligent lighting scheme according to some implementations of the present disclosure.
Figure 5B:
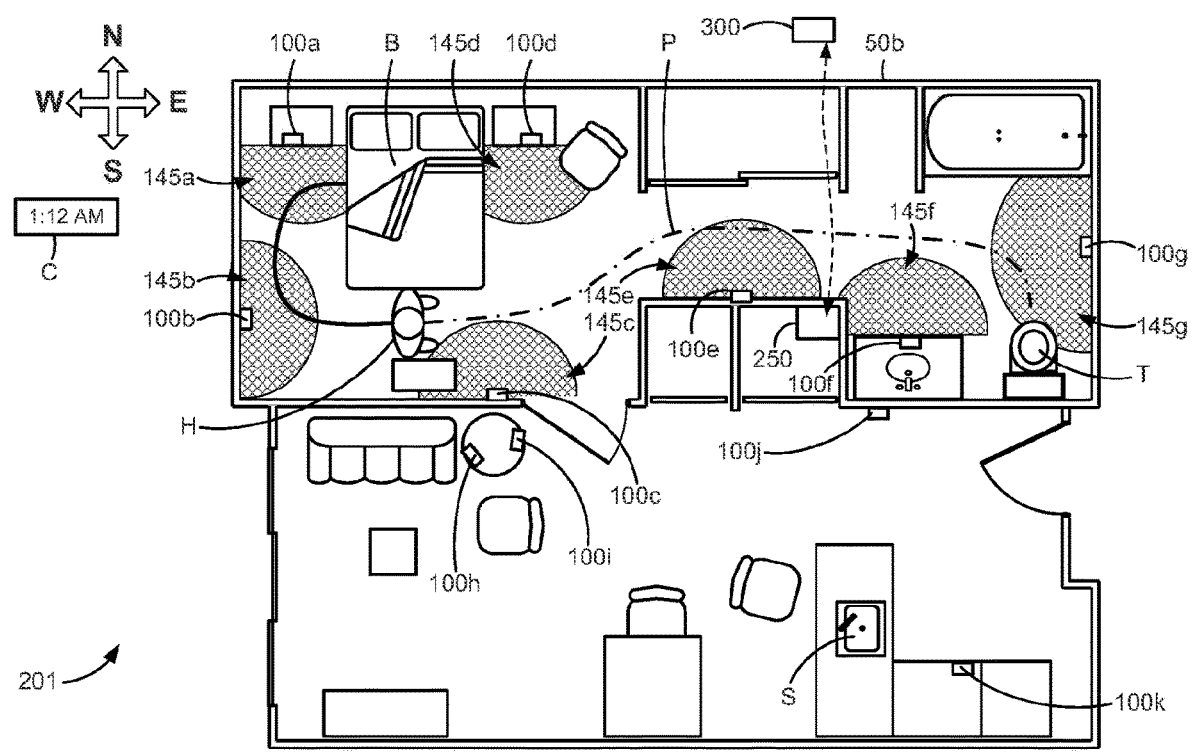
FIG. 5B is a plan schematic illustration of the motion-activated lighting system of FIG. 4 illustrating a second stage of the intelligent lighting scheme of FIG. 5A.
Figure 5C:
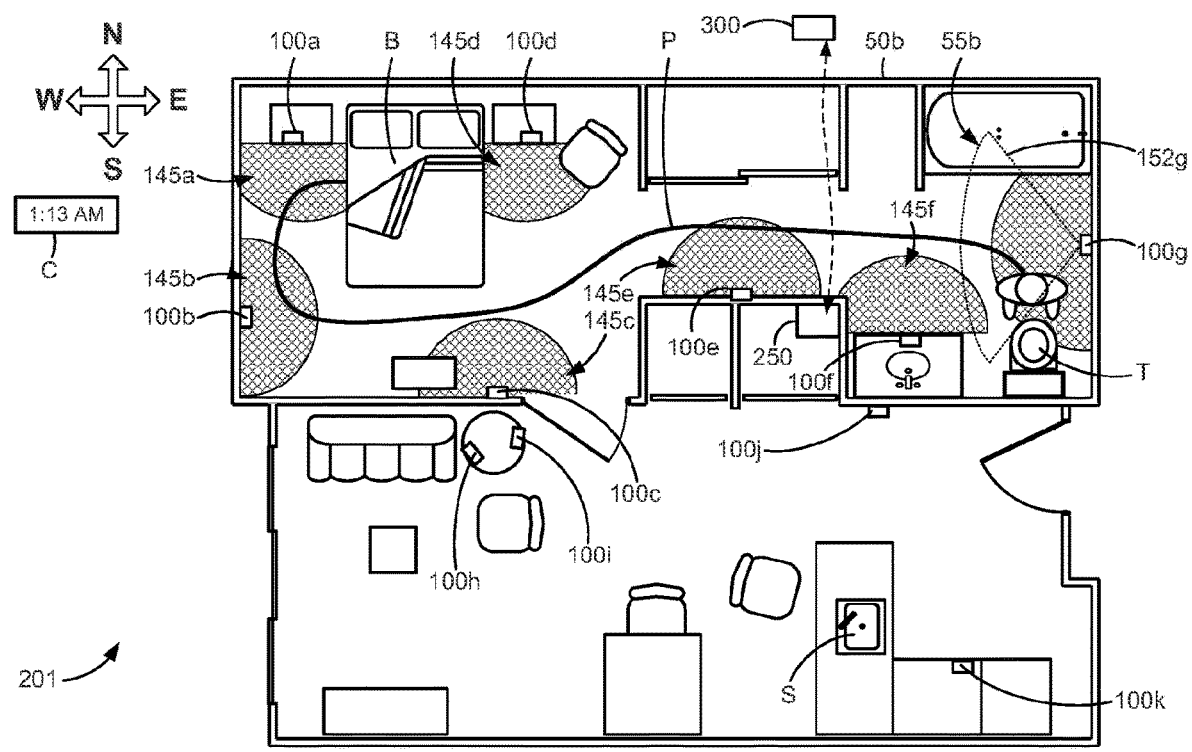
FIG. 5C is a plan schematic illustration of the motion-activated lighting system of FIG. 4 illustrating a third stage of the intelligent lighting scheme of FIG. 5A.

Now referring to FIGS. 5A-5C, an exemplary operation of the motion-activated lighting system 201 is illustrated in the location 50b to show one of the possible intelligent lighting schemes according to some implementations of the present disclosure. As shown in FIG. 5A, the intelligent lighting scheme begins when the human, H, gets out of bed, B, and steps into the sensing range 152a of the first motion-activated lighting unit 100a at 1:12 AM, which is shown by the clock, C. As shown in FIG. 5A, all of the light sources 140 in all of the motion-activated lighting units 100a-k are initially off (e.g., as the human, H, was sleeping).

In this first lighting scheme example of FIGS. 5A-5C, the first detection of motion causes a chain reaction of the light sources 140 that are turned on to light a pathway, P, as shown in FIG. 5B. Specifically, each of the light sources 140 in the motion-activated lighting units 100a-g, which are along the pathway, P, are activated (e.g., turned on in response to an activation signal) as illustrated by the illumination ranges 145a-g being shown (FIGS. 5B and 5C).

In some implementations, in response to the motion sensor 155 of the first motion-activated lighting unit 100a detecting the first motion, a first motion signal is transmitted, via the communications module 120 of the first motion-activated lighting unit 100a, to the local master controller 250. The first motion signal is indicative of the occurrence of the first motion in a first predefined zone 55a. As shown, the first predefined zone 55a is defined by the sensing range 152a of the motion sensor 155 in the first motion-activated lighting unit 100a, which is adjacent to a first side of the bed, B, and generally in front of a first nightstand in the location 50b. In response to the local master controller 250 receiving the first motion signal, the local master controller 250 determines which light sources 140, if any, should be activated (e.g., based on a predicted destination) and then transmits one or more instructions (e.g., one or more activation signals) within the motion-activated lighting system 201 accordingly (e.g., to the motion-activated lighting units along the pathway, P).

The pathway, P, can be lit up by the light sources 140 at the same time or about the same time or in a sequential fashion (e.g., one after the other) until all of the light sources 140 adjacent to the pathway, P are activated (i.e., on). Such a lighted pathway, P, aids the human, H, in seeing/viewing the floor of the location 50b and in safely moving to a predicted destination (e.g., the bathroom/toilet). The predicted destination is based on the time of day/night that the first motion is detected (i.e., 1:12 AM), the location of the motion-activated lighting unit including the motion sensor 155 that detects the first motion (i.e., the first motion-activated lighting unit 100a) in the location 50b, and a known movement pattern.

The known movement pattern can be one of a multitude of known movement patterns associated with the motion-activated lighting system 201. The known movement patterns can be preprogrammed into the motion-activated lighting system 201 (e.g., stored in a memory device of the local master controller 250) and/or learned by the motion-activated lighting system 201 over time by, for example, analyzing movements occurring within the motion-activated lighting system 201. For example, the motion-activated lighting system 201 can learn and/or develop known movement patterns by analyzing generated log data and/or generated additional log data stored in one or more memory devices of, for example, the local master controller 250.

As shown by comparing FIGS. 5A-5C, the human, H, makes its way along the pathway, P, from the first predefined zone 55a, through a series of sensing ranges 152a-152f of the motion-activated lighting units 100a-f, until the Human, H, reaches the predicted destination, here, the toilet, T, in the bathroom, which is the second predefined zone 55b. The second predefined zone 55b is defined by the sensing range 152g of the motion sensor 155 in the seventh motion-activated lighting unit 100g, which is adjacent to the toilet, T. By strategically positioning the motion-activated lighting units 100a-g in the location 50b such that the sensing ranges 152a-152g cover portions of the pathway, P, the motion-activated lighting system 201 is able to confirm that the human, H, is moving along the pathway, P, to the predicted destination (e.g., the toilet, T).

In some implementations, the predicted destination might be wrong and because the motion-activated lighting system 201 can monitor in realtime the movements of the human, H, the motion-activated lighting system 201 can make adjustments to the lighting scheme on the fly. For example, if the motion-activated lighting system 201 detects movement in the sensing range 152a, then sensing range 152b, then sensing range 152c, but instead of detecting the next movement in sensing range 152d, the motion-activated lighting system 201 detects the next movement in sensing range 152i (FIG. 4), then the motion-activated lighting system 201 can determine on the fly in realtime that the predicted destination of the bathroom/toilet was wrong and make adjustments accordingly. For example, in such a scenario, the motion-activated lighting system 201 may deactivate (i.e., turn off) the light sources 140 along the pathway, P, and activate (i.e., turn on) the light sources 140 along an updated or revised pathway (not shown), such as one to the kitchen sink, S.

As shown in FIG. 5C, the human, H, made its way from the bed, B, to the toilet, T, by 1:13 AM and was guided by the light sources 140 of the motion-activated lighting units 100a-g that illuminate the pathway, P. As described, the motion-activated lighting system 201 can continuously monitor movements to determine information. Further, the motion-activated lighting system 201 can determine the absence of a predicted movement or a non-movement or a non-return movement that the motion-activated lighting system 201 expects/predicts based on one or more known movement patterns. For example, not only did the motion-activated lighting system 201 predict correctly in the implementation shown in FIGS. 5A-5C that the human, H, woke up from bed, B, and was going to the toilet, T, but the motion-activated lighting system 201 can also predict that the human, H, will make a corresponding return trip along the pathway, P, in a reverse order and get back into bed, B.

Based at least in part on the known movement patterns, the motion-activated lighting system 201 can predict and/or expect that the human, H, will return to the bed, B, and thus cause a motion to be sensed in the first predetermined zone 55a, within a preset time (e.g., within five minutes, within ten minutes, etc.). As such, the motion-activated lighting system 201 will transmit (e.g., in a wireless and/or wired fashion), via the local master controller 250, an alarm signal to the remote server 300 in response to the motion-activated lighting system 201 not detecting a return movement in the first predetermined zone 55a within the preset time. The alarm signal may indicate that the human, H, is experiencing a potential non-normal behavior as described herein.

In some implementations, prior to the alarm signal being transmitted, the motion-activated lighting system 201 permits the human, H, to cancel the alarm signal by, for example, prompting the human, H, to activate an "all-clear" signal, by, for example, pulling a cord, pressing a button on a pendant or phone, moving in a predetermined zone away from their current predetermined zone (e.g., moving from the bathroom to the bedroom or to the kitchen), etc. The prompting may occur via one or more audio instructions played by the motion-activated lighting system 201 using one or more audio speakers (not shown) of the motion-activated lighting system 201. Additionally or alternatively, prompting may occur via the flashing of one or more of the light sources 140 indicating an alarm signal is about to be transmitted. In some such implementations, the flashing of the light sources by include the flashing of yellow colored light or orange colored light indicating the imminent transmission of an alarm signal.

In some implementations, when the alarm signal is transmitted, the motion-activated lighting system 201 also takes one or more other actions. For example, in some implementations, prior to the alarm signal being transmitted, the motion-activated lighting system 201 can cause one or more of the light sources 140 to be activated (turn on). In some implementations, all of the light sources 140 are activated to aid any first responders in seeing within the location 50b. In some implementations, the lights adjacent to the front door or entryway of the location 50b are activated. In some implementations, one or more of the light sources 140 is activated to emit an "alarm color" such as red colored light, which can aid first responders in knowing that they are in the correct location that corresponds to the alarm signal being responded to.

Figure 6A:
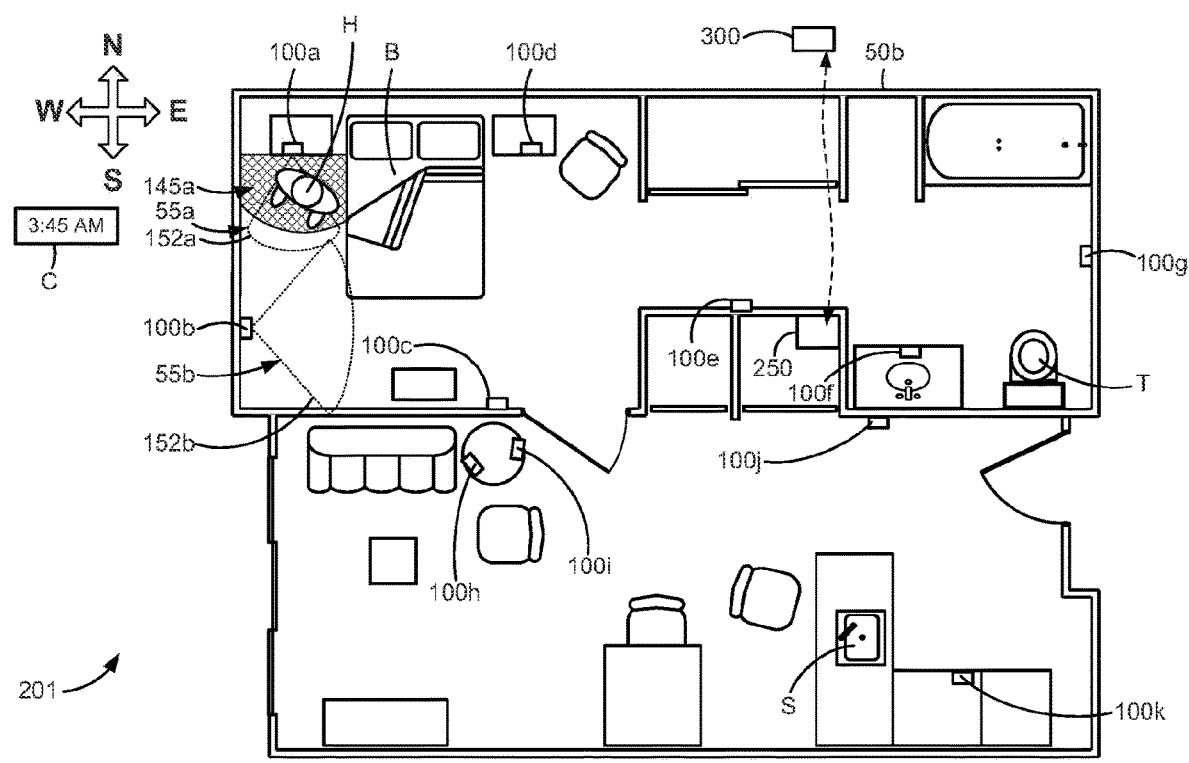
FIG. 6A is a plan schematic illustration of the motion-activated lighting system of FIG. 4 illustrating a first stage of another intelligent lighting scheme according to some implementations of the present disclosure.
Figure 6B:
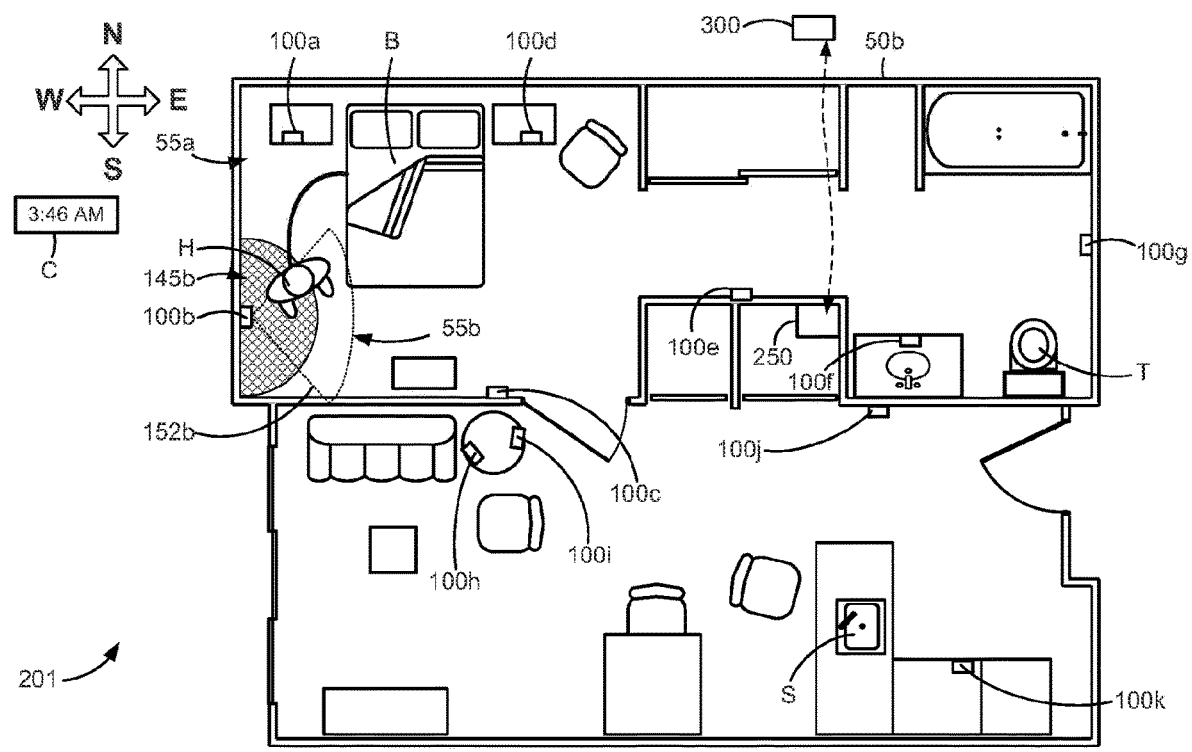
FIG. 6B is a plan schematic illustration of the motion-activated lighting system of FIG. 4 illustrating a second stage of the intelligent lighting scheme of FIG. 6A.

Now referring to FIGS. 6A and 6B, another exemplary operation of the motion-activated lighting system 201 is illustrated in the location 50b to show another one of the possible intelligent lighting schemes according to some implementations of the present disclosure. As shown in FIG. 6A, the intelligent lighting scheme begins when the human, H, gets out of bed, B, and steps into the sensing range 152a of the first motion-activated lighting unit 100a at 3:45 AM, which is shown by the clock, C. As shown in FIG. 6A, the light source 140 in the first motion-activated lighting unit 100a is activated (illustrated by line hatching in the illumination range 145a) and all of other light sources 140 in the motion-activated lighting units 100b-k remain off.

In this second lighting scheme example of FIGS. 6A and 6B, the first detection of motion does not cause a chain reaction of the light sources 140 like the example of FIGS. 5A-5C. Rather, this second example is a one-to-one lighting scheme, where the light sources 140 turn on when motion is detected a predefined zone associated with that specific light source 140 and then turn off when motion is detected in a different predefined zone not associated with that specific light source.

In some implementations, in response to the motion sensor 155 of the first motion-activated lighting unit 100a detecting the first motion and the ambient light being below a set threshold level (e.g., less than five lumens per square foot), (i) the light source 140 of the first motion-activated lighting unit 100a is activated by the microcontroller 110 of the first motion-activated lighting unit 100a and (ii) a first motion signal is transmitted, via the communications module 120 of the first motion-activated lighting unit 100a, to the local master controller 250. The first motion signal can be indicative of the occurrence of the first motion in a first predefined zone 55a and/or can indicate to that the light source 140 of the first motion-activated lighting unit 100a is activated.

As the human, H, continues to move and leaves the first predetermined zone 55a defined by the first sensing range 152a and enters into the second predetermined zone 55b (FIG. 6B) defined by the second sensing range 152b, the light source 140 in the first motion-activated lighting unit 100a is deactivated (illustrated by line hatching in the illumination range 145a being removed in FIG. 6B) and the light source 140 in the second motion-activated lighting unit 100b is activated (illustrated by line hatching in the illumination range 145b shown in FIG. 6B). Specifically, for example, in response to the motion sensor 155 of the second motion-activated lighting unit 100b detecting a second motion in the second predefined zone 55b and the ambient light being below a set threshold level (e.g., less than five lumens per square foot), (i) the light source 140 of the second motion-activated lighting unit 100b is activated by the microcontroller 110 of the second motion-activated lighting unit 100b (ii) a second motion signal is transmitted, via the communications module 120 of the second motion-activated lighting unit 100b, to the local master controller 250, and (iii) a deactivation signal is transmitted, from the local master controller 250 to the communications module 120 of the first motion-activated lighting unit 100a with instructions for the microcontroller 110 of the first motion-activated lighting unit 100a to deactivate the light source 140 of the first motion-activated lighting unit 100a. Alternatively, the communications module 120 of the second motion-activated lighting unit 100b can communicate directly with the communications module 120 of the first motion-activated lighting unit 100a.

Various other lighting schemes are contemplated. For example, instead of the light source 140 of the first motion-activated lighting unit 100a being deactivated in response to the second motion being sensed in the second predefined zone 55b, the light source 140 can remain activated for a preset period of time (e.g., thirty seconds, one minute, five minutes, etc.) regardless of where the human, H, moves subsequently.

Figure 7A:
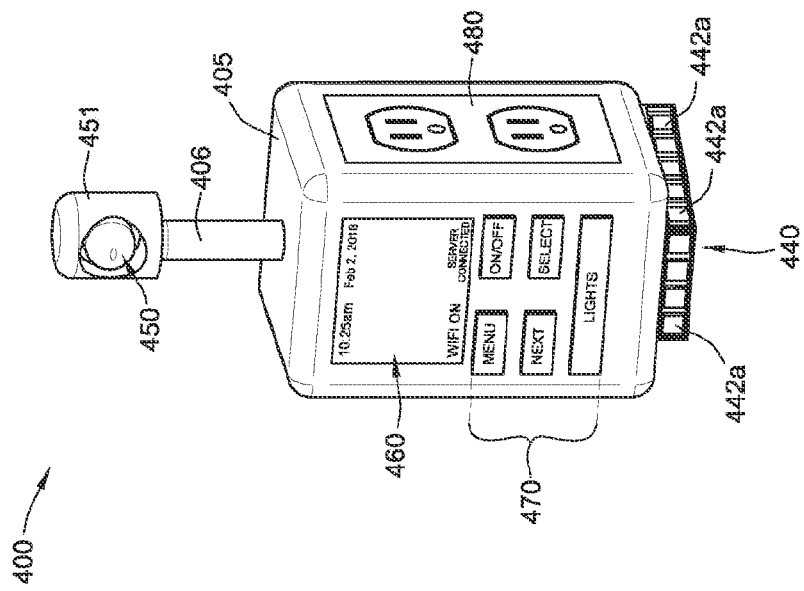
FIG. 7A is a front perspective view of a motion-activated lighting unit with a sensor housing in a retracted position according to some implementations of the present disclosure.
Figure 7B:
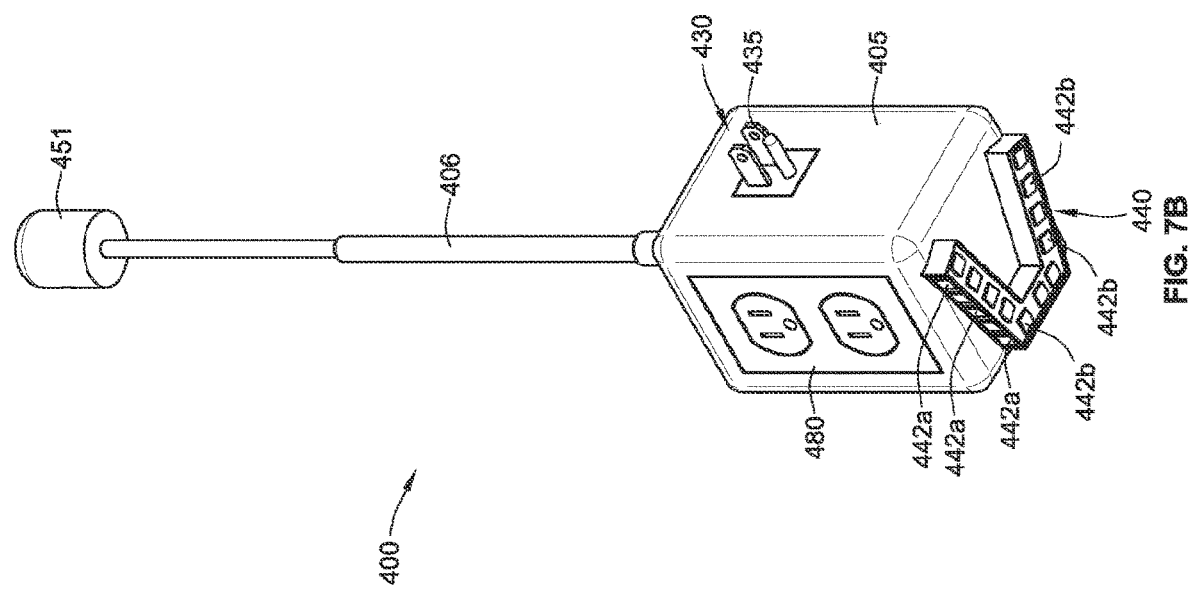
FIG. 7B is a rear perspective view of the motion-activated lighting unit of FIG. 7A with the sensor housing in an extended position.

Now referring to FIGS. 7A and 7B, a motion-activated lighting unit 400 is shown. The motion-activated lighting unit 400 is the same as, or similar to, the motion-activated lighting unit 100 described above. The motion-activated lighting unit 400 includes a microcontroller (not shown), a communications module (not shown), a power module 430 (partially shown in FIG. 7B), a light source 440, and sensors 450, which are the same as, or similar to, the microcontroller 110, the communications module 120, the power module 130, the light source 140, and the sensors 150 of the motion-activated lighting unit 100.

The motion-activated lighting unit 400 has a main housing 405 and a sensor housing 451, which are coupled together via rigid member 406, which may or may not be a telescoping rigid member. The microcontroller (not shown), the communications module (not shown), and the power module 430 (partially shown in FIG. 7B), are each contained within the main housing 405 of the motion-activated lighting unit 400. The sensors 450 are contained within the sensor housing 451. The sensors 450 include a motion sensor and an ambient light sensor, which are the same as, or similar to, the motion sensor 155 and the ambient light sensor 157 of the motion-activated lighting unit 100.

The motion-activated lighting unit 400 further includes a display device 460, input devices 470, and a built-in power outlet 480. The motion-activated lighting unit 400 is designed to be directly plugged into a standard electrical outlet, via the plug 435 of the power module 430. As most standard electrical outlets are positioned about eighteen inches off the floor, to avoid sensing motion of pets (e.g., dogs, cats, etc.), the sensors 450 can be moved vertically, relative to the main housing 405, by pulling the sensor housing 451 up and away from the main housing 405, thereby causing the telescoping, rigid member 406 to extend and position the sensors 450 relatively higher (compare FIG. 7B, higher, with FIG. 7A, lower). The motion sensor and the ambient light sensor are contained within the sensor housing 451 and are electrically coupled to the microcontroller (not shown) in the main housing 405 via one or more wires (not shown) extending inside the telescoping, rigid member 406.

The light source 440 is positioned on an underside of the main housing 405 such that the light source 440 is able provide downward illumination of a floor area in at least a portion of a predefined zone associated with the motion-activated lighting unit 400. For example, the predefined zone associated with the motion-activated lighting unit 400 can be defined by the sensing range of the motion sensor of the sensors 450 in the sensor housing 451. The light source 440 includes a first set of lights 442a and a second set of lights 442b. The first set of lights 442a is positioned generally around an exterior side surface of the light source 440 to generally provide an outward illumination of light, whereas the second set of lights 442b is positioned generally on an exterior bottom surface of the light source 440 to generally provide a downward illumination of light.

Figure 8:
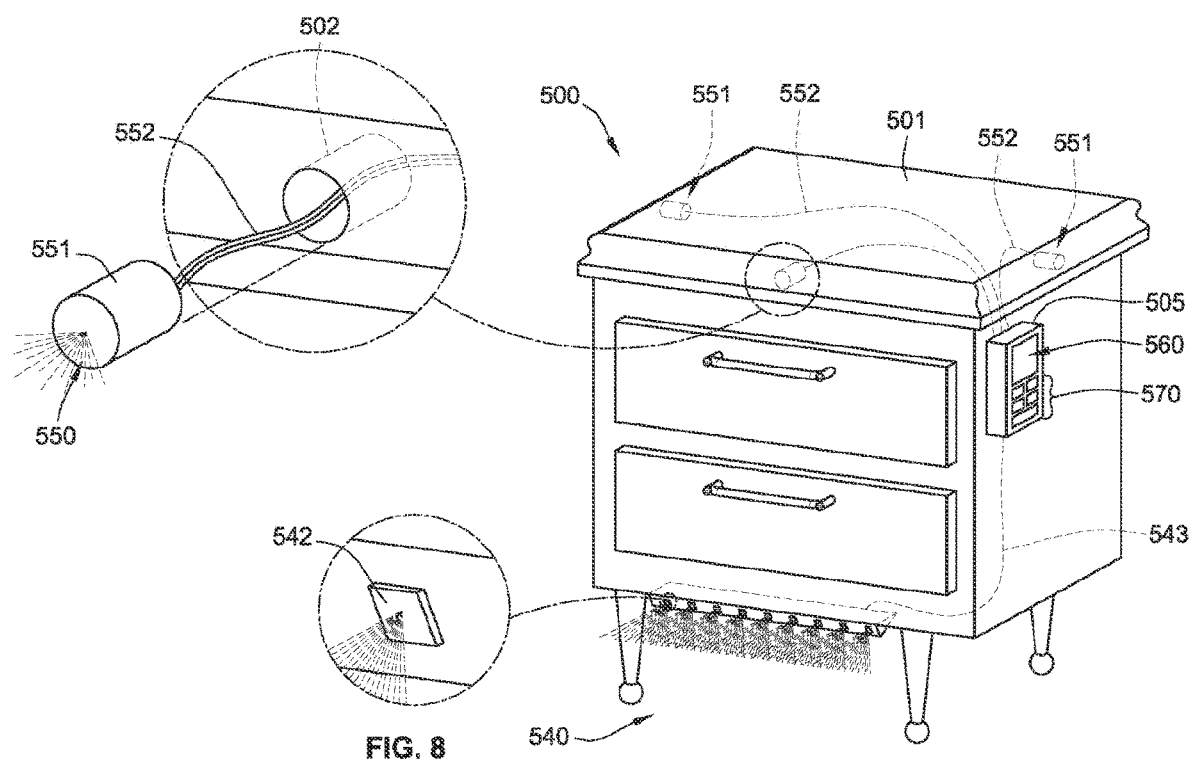
FIG. 8 is a front perspective view of a motion-activated lighting unit incorporated into and/or on an item of furniture according to some implementations of the present disclosure.

Now referring to FIG. 8, a motion-activated lighting unit 500 is shown as being incorporated into and/or on a nightstand 501 (i.e., an item of furniture). While the motion-activated lighting unit 500 is shown as being incorporated into and/or on a single nightstand 501, it is contemplated that the motion-activated lighting unit 500 can be incorporated into and/or on any number of items of furniture (e.g., one item, two items, three items, etc.).

The motion-activated lighting unit 500 is the same as, or similar to, the motion-activated lighting unit 100 described above. The motion-activated lighting unit 500 includes a microcontroller (not shown), a communications module (not shown), a power module (not shown), a light source 540, and sensors 550, which are the same as, or similar to, the microcontroller 110, the communications module 120, the power module 130, the light source 140, and the sensors 150 of the motion-activated lighting unit 100.

As shown, the motion-activated lighting unit 500 has a main housing 505 that is coupled to the side of the nightstand 501; however, the main housing 505 can be coupled to any portion of the nightstand 501 or positioned in an relationship relative to the nightstand 501 (e.g., the main housing 505 can be coupled to the back of the nightstand 501, resting on the floor, etc.). The motion-activated lighting unit 500 further includes a display device 560 and input devices 570 coupled to the main housing 505.

The microcontroller (not shown), the communications module (not shown), and the power module (not shown), are each contained within the main housing 505 of the motion-activated lighting unit 500. Although not shown, the power module of the motion-activated lighting unit 500 extends from the main housing 505 via an electrical wire/plug that is plugged into a standard electrical outlet (e.g., positioned behind the nightstand 501).

The motion-activated lighting unit 500 includes three sensor housings 551. Each of the sensor housings 551 includes a motion sensor and an ambient light sensor therein, which are the same as, or similar to, the motion sensor 155 and the ambient light sensor 157 of the motion-activated lighting unit 100. While three sensor housings 551 are shown, any number of sensor housings 551 and/or sensors 550 is contemplated as being included in the motion-activated lighting unit 500.

Each of the sensor housings 551 is built into the nightstand 501. Specifically, as shown, the nightstand (if, for example, made of wood) can be drilled and/or fabricated to include one or more slots 502 sized and shaped to fit each of the sensor housings 551 therein. In some implementations, the slot 502 is sized such that a front surface of the sensor housing 551 (e.g., a lens of the motion sensor and/or of the ambient light sensor) is flush with the nightstand 501 when the sensor housing 551 is fully seated therein. In some implementations, the front surface of the sensor housing 551 is smoked and/or colored to better blend in with the color of the item of furniture to which it is incorporated (i.e., built into). The slots 502 are included in the top portion of the nightstand 501 such that the sensors 550 are generally positioned high enough off the floor (e.g., more than one foot above the floor, more than eighteen inches above the floor, more than two feet above the floor, etc.) to avoid sensing motion of pets (e.g., dogs, cats, etc.). Extending from a rear end of each of the sensor housings 551 are one or more wires 552 that electrically couple the sensors 550 in each of the sensor housings 551 with the microcontroller (not shown) in the main housing 505 of the motion-activated lighting unit 500.

The light source 540 is positioned on an underside of the nightstand 501 such that the light source 540 is able provide downward illumination of a floor area in at least a portion of a predefined zone associated with the motion-activated lighting unit 500. For example, the predefined zone associated with the motion-activated lighting unit 500 can be defined by the sensing range of the motion sensor of one or more of the sensors 550 in the sensor housings 551. The light source 540 includes a set of lights 542 that is positioned to generally provide a downward illumination of light. The light source 540 is electrically coupled with the microcontroller (not shown) in the main housing 505 of the motion-activated lighting unit 500 via one or more wires 543.

Figure 9:
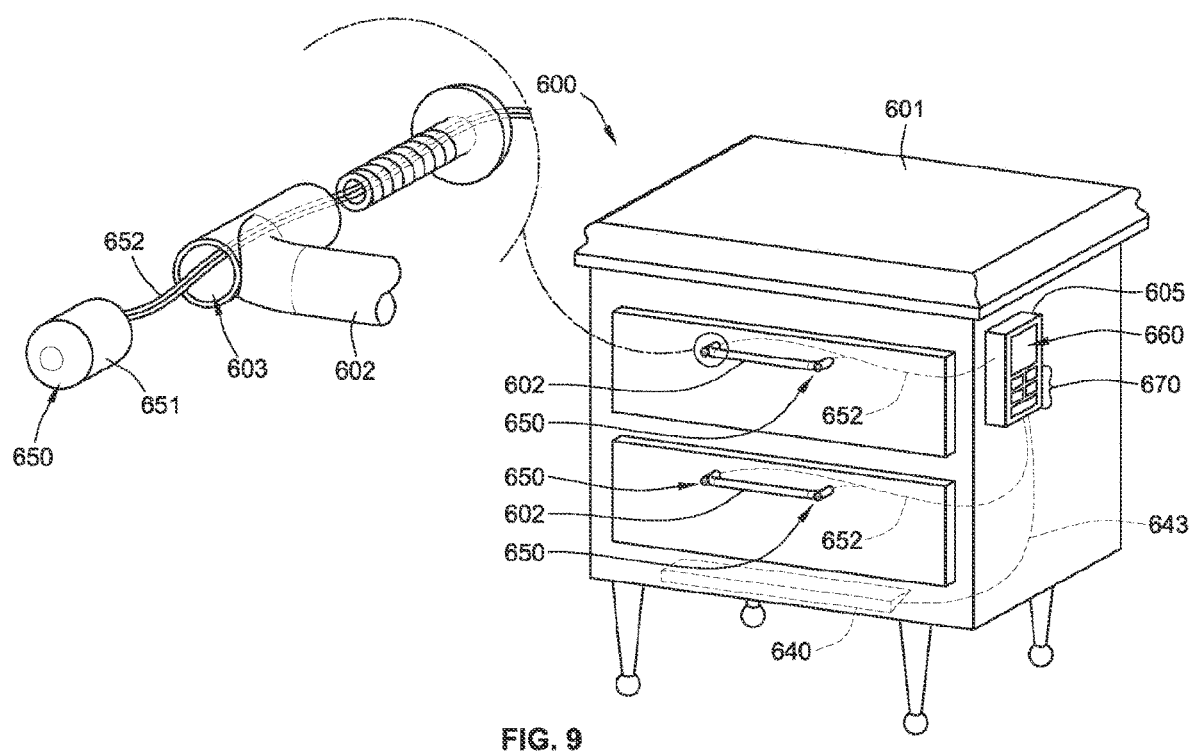
FIG. 9 is a front perspective view of a motion-activated lighting unit incorporated into and/or on an item of furniture according to some implementations of the present disclosure.

Now referring to FIG. 9, a motion-activated lighting unit 600 is shown as being incorporated into and/or on a night stand 601 (i.e., an item of furniture). The motion-activated lighting unit 600 is the same as, or similar to, the motion-activated lighting units 100, 500 described above. The motion-activated lighting unit 600 includes a microcontroller (not shown), a communications module (not shown), a power module (not shown), a light source 640, and sensors 650, which are the same as, or similar to, the microcontroller 110, the communications module 120, the power module 130, the light source 140, and the sensors 150 of the motion-activated lighting unit 100.

As shown, the motion-activated lighting unit 600 has a main housing 605 that is coupled to the side of the nightstand 601; however, the main housing 605 can be coupled to any portion of the nightstand 601 or positioned in an relationship relative to the nightstand 601 (e.g., the main housing 605 can be coupled to the back of the nightstand 601, resting on the floor, etc.). The motion-activated lighting unit 600 further includes a display device 660 and input devices 670 coupled to the main housing 605.

The microcontroller (not shown), the communications module (not shown), and the power module (not shown), are each contained within the main housing 605 of the motion-activated lighting unit 600. Although not shown, the power module of the motion-activated lighting unit 600 extends from the main housing 605 via an electrical wire/plug that is plugged into a standard electrical outlet (e.g., positioned behind the nightstand 601).

The motion-activated lighting unit 600 includes four sensor housings 651. Each of the sensor housings 651 includes a motion sensor and an ambient light sensor therein, which are the same as, or similar to, the motion sensor 155 and the ambient light sensor 157 of the motion-activated lighting unit 100. While four sensor housings 651 are shown, any number of sensor housings 651 and/or sensors 650 is contemplated as being included in the motion-activated lighting unit 600.

Each of the sensor housings 651 is built into the nightstand 501. Specifically, as shown, each of the sensor housings 651 is built into a handle 602 of the nightstand 501. In some implementations, the handle 602 is modified and/or fabricated to include one or more slots 603 that accommodate one or more sensor housings 651 therein. In some implementations, the front surface of the sensor housing 651 is smoked and/or colored to better blend in with the color of the handle 602 to which it is incorporated (i.e., built into). Extending from a rear end of each of the sensor housings 651 are one or more wires 652 that electrically couple the sensors 650 in each of the sensor housings 651 with the microcontroller (not shown) in the main housing 605 of the motion-activated lighting unit 600.

The light source 640 is positioned on an underside of the nightstand 601 such that the light source 640 is able provide downward illumination of a floor area in at least a portion of a predefined zone associated with the motion-activated lighting unit 600. For example, the predefined zone associated with the motion-activated lighting unit 600 can be defined by the sensing range of the motion sensor of one or more of the sensors 650 in the sensor housings 651. The light source 640 is electrically coupled with the microcontroller (not shown) in the main housing 605 of the motion-activated lighting unit 600 via one or more wires 643.

As discussed above, the systems of the present disclosure are able to transmit (e.g., from the local master controller 250 to the remote server 300) an alert signal. The alert signal can be as simple as a message to a third party (e.g., on-duty nurse, security guard, receptionist, etc.) that conveys non-actionable information. For example, an alert signal might convey that a human/patient/resident is out of bed, or the resident is in the bathroom, or the resident is in the kitchen. This information is non-actionable because there is nothing for the third party to do at this point. It is only when an alarm is triggered and an alarm signal is transmitted (e.g., from the local master controller 250 to the remote server 300) that the third party needs to act. For example, an alarm may be triggered if a human/patient/resident gets out of bed, goes to the bathroom, and does not return to bed or does not leave the bathroom after a predetermined amount of time (e.g., ten minutes, fifteen minutes, thirty minutes, etc.). For an alarm to trigger, the scenario might also be time dependent (e.g., only triggerable between 10 PM and 6 AM). For example, a resident may get out of bed at 11:30 PM and walk through the hallway and into the bathroom. The system tracks these motions via a set of motion-activated lighting units positioned strategically in each of the relevant rooms (e.g., bedroom, hallway, bathroom, kitchen, living room, dining room, den, etc.). As the resident moves from the bedroom, into the hallway, and into the bathroom, each respective motion-activated lighting unit transmits a motion signal either directly to the third party monitor or via a local master controller, which may simply indicates motion in the residence, which room, and the time. It is not until, for example, the resident fails to return to bed within a predetermined amount of time (which can be a learned amount of time for each resident depending on the resident's learned patterns) that an alarm is triggered and an alarm signal is transmitted to the third party monitor for one or more actions to be taken (e.g., calling 911, sending the on-duty nurse to the residence, sending a doctor to the residence, sending an emergency response person to the residence, conducting a well-being check, etc.).

In some implementations, the motion-activated lighting units of the present disclosure are provided as a kit of materials that can be retrofitted into and/or on any item of furniture (e.g., nightstand, desk, couch, chair, bed, cabinet, toilet, etc.).

The motion-activated lighting units of the present disclosure can be self-installed by any user and can be a plug-and-play system where each of the motion-activated lighting units needs to only be plugged into the wall to provide power and then the motion-activated lighting units automatically start-up and communicatively connect to each other (e.g., directly and/or through a local master controller) such that the motion-activated lighting units of the present disclosure can self-establish/create/form a motion-activated lighting system of the present disclosure to operate as described herein.

In some implementations, the light sources of the present disclosure can be installed simply by peeling a protecting layer off one side of the light source, thereby exposing a sticky layer, sticking the light source to an underside of an item of furniture, and plugging the light source into a source of power (e.g., directly into a wall outlet or into the main housing of the motion-activated lighting unit such that the light source is powered via the power module in the main housing).

Figure 10:
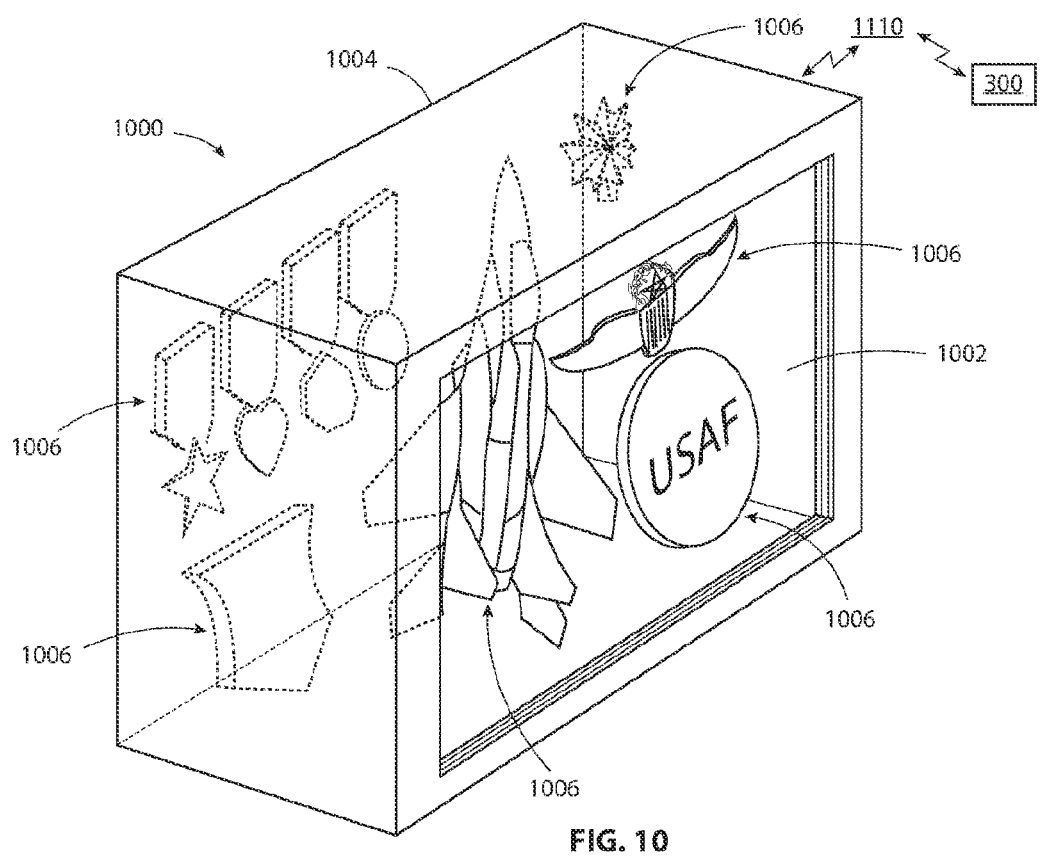
FIG. 10 is an isometric view of a memory box that houses tangible items that are rendered visible or obscured by operation of a transparent touch-sensitive video display according to some implementations of the present disclosure.

FIG. 10 illustrates an information system 1000 that includes a housing 1004 having a cavity configured to receive tangible items 1006 therein. For ease of discussion, the information system 1000 shown in FIG. 10 can be referred to herein as a memory box. The tangible items can include items of memorabilia or other personal significance to a person. The housing 1004 can be installed near a door frame for an entrance door to a room or apartment in a living facility, for example. The housing 1004 is visible as one approaches the entrance door so that the tangible items inside the housing 1004 can be seen.

A transparent, touch-sensitive organic light emitting device (OLED) display 1002 is positioned over the cavity and is configured such that when pixels of the OLED display are black, the tangible items 1006 behind the black pixels are visible through the transparent OLED display 1002. The OLED display 1002 can be configured to detect touches made on its surface or can include a separate transparent, touch-sensitive overlay that is configured to detect one or more touches made on the overlay.

Figure 12:
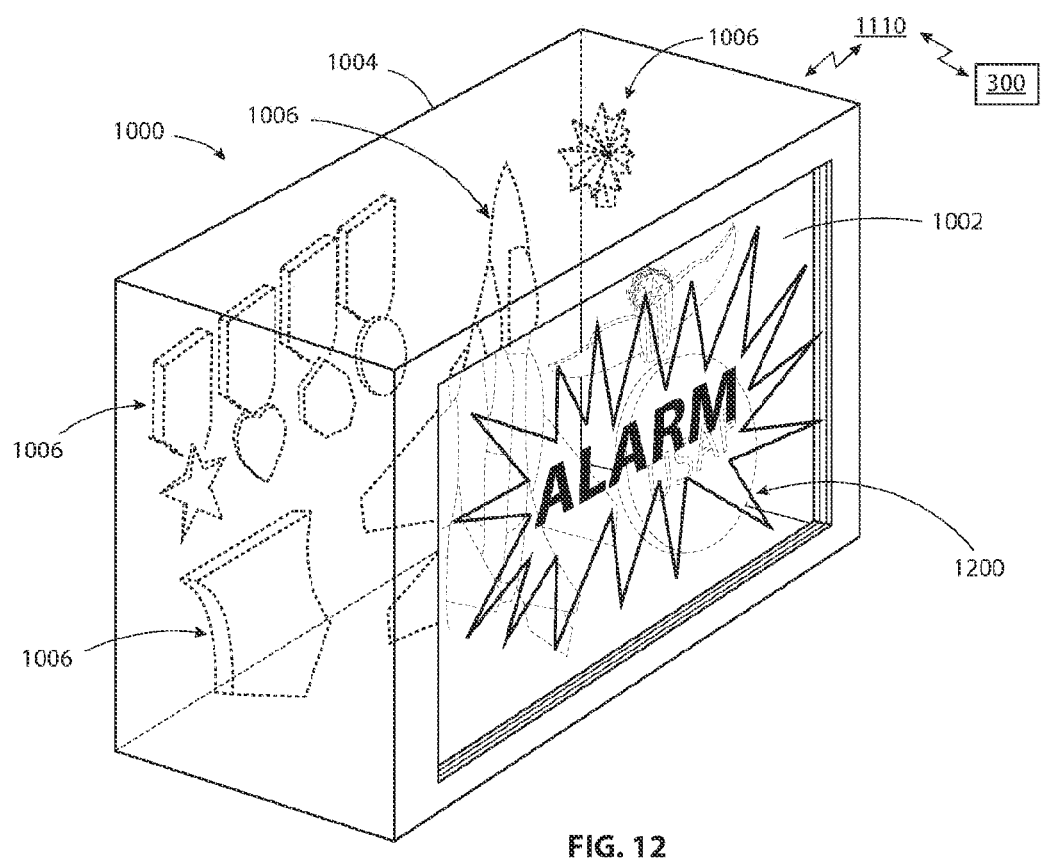
FIG. 12 illustrates an example flashing or pulsing alarm that can be displayed on the transparent touch-sensitive video display shown in FIG. 10, which obscures the tangible items housed in the memory box while the alarm is being displayed, according to some implementations of the present disclosure.

Although not shown in FIG. 10, the information system 1000 includes components like those described above, including a communications module, such as the communications module 120, and a memory device, which can be incorporated into an electronic controller, such as the microcontroller 110. The electronic controller 110 is coupled to the OLED display 1002 and to the communications module. The controller 110 is programmed to receive via the communications module 120 from a remote server, such as the remote server 300, an alarm signal. In response to receiving the alarm signal, the controller 110 causes the OLED display 1002 to change its state to indicate an alarm condition 1200 on the OLED display 1002, such as shown in FIG. 12. The alarm condition 1200 can, for example, include flashing or pulsing the display 1002 a red color, displaying alarm 1200 or other indicia to indicate an alarm condition 1200 inside the room. In this disclosure, alarms can be raised inside the room, such as by a resident who activates a pendant worn on the body or pulls a cord to activate an alarm, or alarms can indicate a problem that is common to an entire facility, such as fire alarms, inclement weather alarms, and the like.

Figure 13:
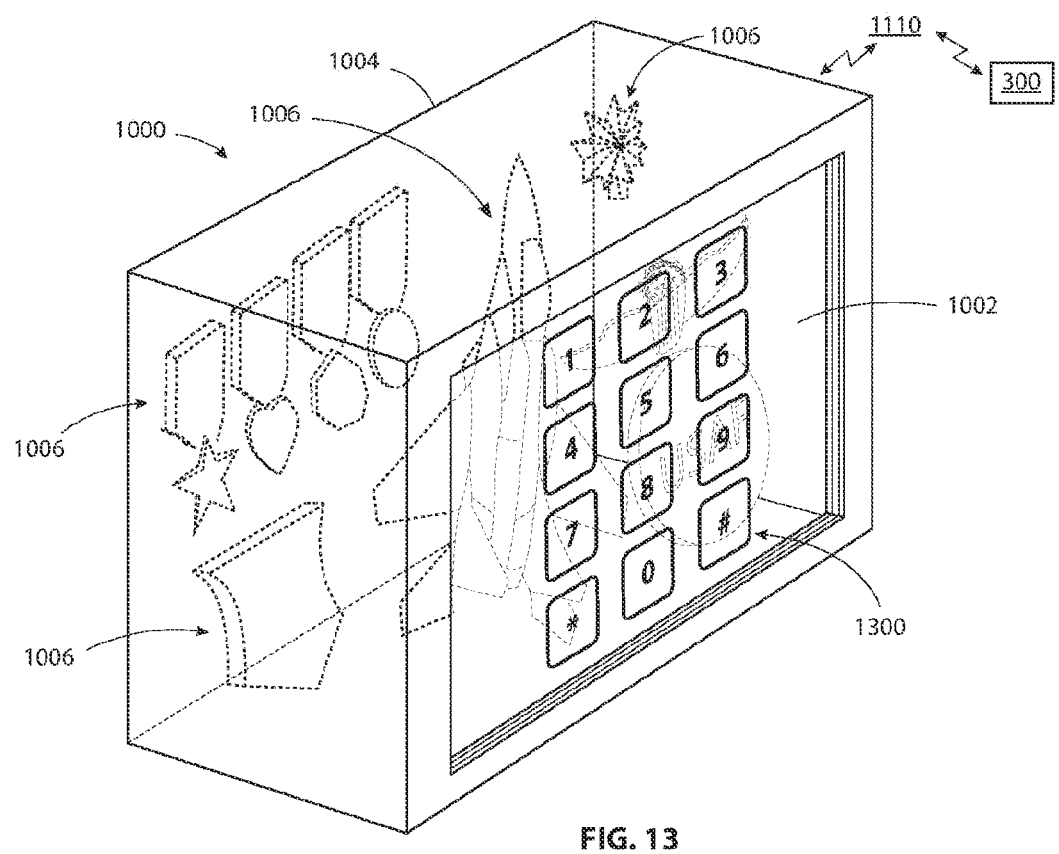
FIG. 13 illustrates an example keypad that can be displayed on the transparent touch-sensitive video display shown in FIG. 10, which can be configured to receive an input from a caregiver to check in or check out of a resident's room, according to some implementations of the present disclosure.

A caregiver can check in and check out of a resident's room using the touch-sensitive OLED display 1002, which can display a keypad 1300, such as shown in FIG. 13. The controller 110 can be programmed to detect an input made on a corner of the touch-sensitive display 1002, for example, to cause the display 1002 to display the keypad 1300. The caregiver inputs a code or PIN on the keypad, which is communicated to the remote server 300 via the communications module 120. The caregiver can check in and out of the room by inputting the caregiver's unique code or PIN assigned to that caregiver.

Figure 11:
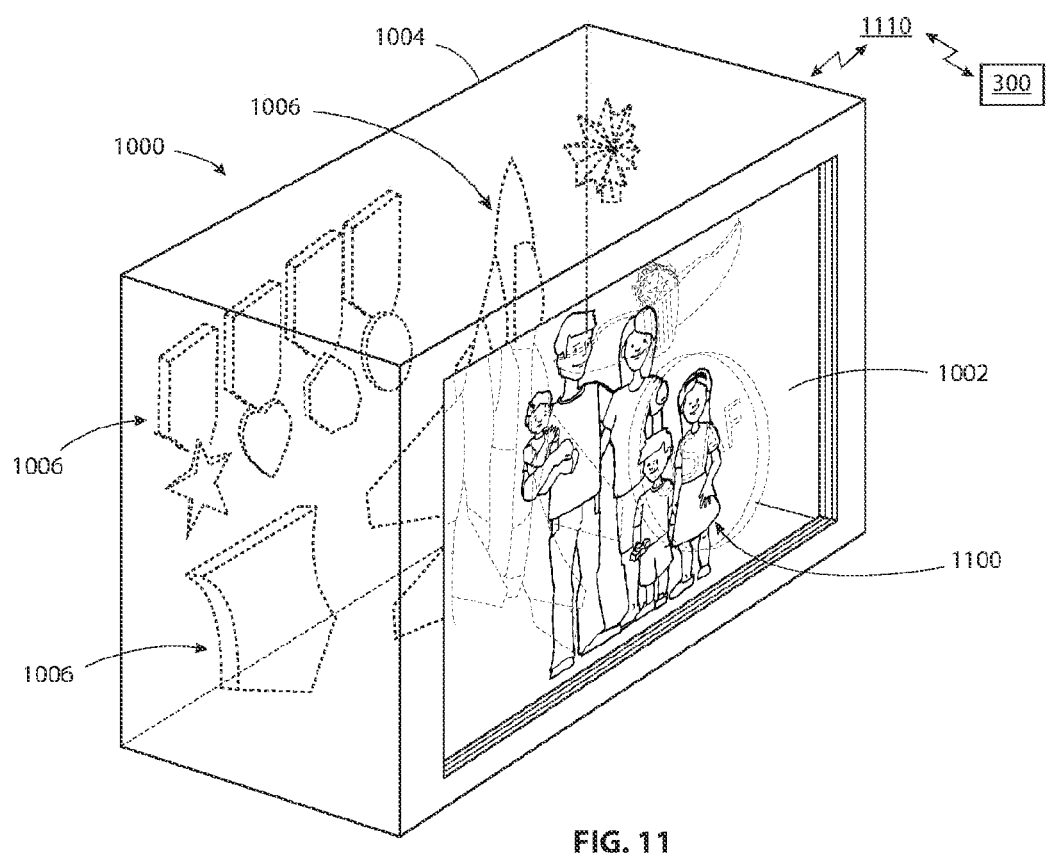
FIG. 11 illustrates an example image displayed on the transparent touch-sensitive video display shown in FIG. 10, which obscures the tangible items housed in the memory box while the image is being portrayed, according to some implementations of the present disclosure.

When the display 1002 is not indicating an alarm or displaying the keypad, at other times, the display 1002 can be configured to display a sequences of images 1100, such as shown in FIG. 11, stored in the memory device. For example, the images 1100 can be photographs of persons, places, or events important or having sentimental value or particular importance to the resident of the room. When the transparent OLED display 1002 is displaying images, including an alarm and keypad, the tangible items 1006 inside the housing 1004 can be rendered partially or completely obscured. Certain pixel areas of the display 1002 can be made black to allow the tangible items 1006 behind the black pixels to be seen through them.

The information system 1000 can include a direction of movement sensor, similar to the sensor 155 described above, configured to detect a direction of movement across the sensor 155. The controller 110 can be configured to communicate via the communications module 120 a signal indicative of the sensed direction of movement to the remote server 300.

The controller 110 can be programmed to indicate via the OLED display 1002 whether a room, an entrance door frame near which the housing is positioned, is occupied by a human resident. For example, when the display 1002 is displaying the sequence of images, this can indicate that the resident is inside the room. However, when the OLED display 1002 is displaying black pixels so that the tangible items 1006 can be seen through the display 1002, this can indicate that the resident is out of the room. These are non-limiting examples of how the transparent display 1002 can be further leveraged to indicate the presence or absence of the resident from the room. One or more light sources can be present inside the housing 1004 to illuminate the tangible items 1006 to make them more visible through the transparent OLED display 1002, particularly at nighttime.

The controller 110 can be programmed to indicate via the OLED display 1002 whether a room, an entrance door frame near which the housing 1004 is positioned, is occupied by a human resident. The OLED display 1002 can indicate that the room is occupied by displaying the sequence of images (such as shown in FIG. 11), and the OLED display 1002 can indicate that the room is not occupied by turning the pixels of the OLED display black so that the tangible items 1006 are visible through the transparent OLED display 1002, such as shown in FIG. 10.

The controller 110 can be programmed to receive via the communications module 120 from the remote server 300 a facility-wide emergency alarm signal. In response, the OLED display 1002 changes its state to indicate an emergency alarm condition (not shown) on the OLED display 1002 that differs from the alarm condition 1200.

For example, if there is a fire or smoke, an indicia indicating a fire or smoke condition can be displayed on the OLED display 1002, and the state of the OLED display 1002 can include an arrow or other indicia indicating a direction of travel to show an evacuation direction of travel during the emergency alarm condition. The emergency alarm condition and the arrow can be pulsed or flashed in a repeating, alternating pattern so that both the type of alarm and the direction of evacuation can be indicated. In a facility having many rooms, all of the corresponding information systems 1000 can show in a coordinated manner an evacuation flow throughout the facility, even on multiple floors.

The direction of movement sensor 155 can be used to determine whether someone has entered or left the room. An entering timer can be triggered when the caregiver inputs a PIN or code on the keypad 1300 of the display 1002, and the entering timer can be stopped when the direction of movement sensor 155 detects a direction of movement indicating a movement into the room. The controller 110 can send a corresponding signal to the remote server 300 indicating that the caregiver has entered the room. Correspondingly, when the direction of movement sensor 155 detects that someone has left the room, a departing timer is started until the caregiver inputs the PIN or code on the keypad 1300. This can help differentiate who left the room—the caregiver or the resident. If the caregiver does not input the PIN or code within a predetermined period of time for the departing timer, then either the caregiver neglected to do so, or the resident left the room. Either way, the controller 110 sends a signal to the remote server 300 indicating that the departing timer expired without an expected PIN or code having been inputted.

Figure 14:
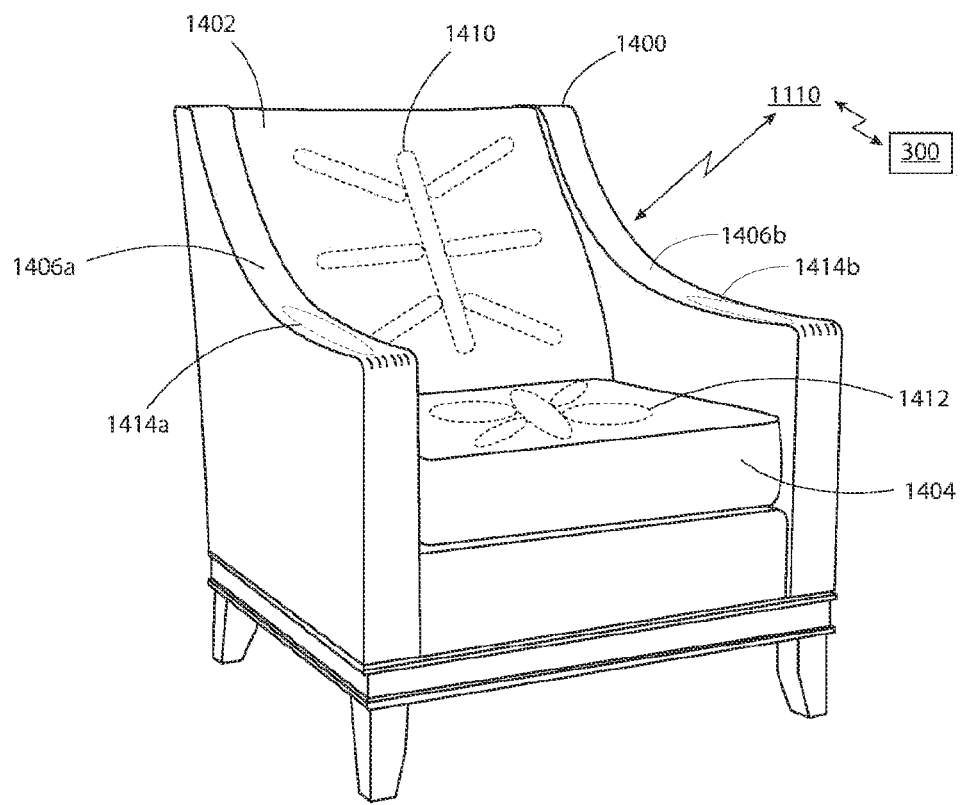
FIG. 14 illustrates an isometric view of an example armchair having an array of pressure-sensitive sensors in the chair seat, back, and armrests, just beneath the outer covering of the chair, according to some implementations of the present disclosure.

Turning to FIG. 14, a chair 1400, which is part of a passive biometric capture system, is shown. The passive biometric capture system can passively track movements of people about a space without the use of any cameras and without requiring the people being tracked to intentionally provide any biometric that differentiates one person from another. The passive biometric system leverages furniture as sensors to passively capture biometrics about a person to track them and to differentiate them from others who use the same furniture and space. The chair 1400 includes an array of pressure-sensitive sensors 1410 in a chair back 1402 of the chair 1400, an array of pressure-sensitive sensors 1412 in a chair seat 1404 of the chair 1400, an array of pressure-sensitive sensors 1414a in a first armrest 1406a of the chair 1400, and an array of pressure-sensitive sensors 1414b in a second armrest 1406b of the chair 1400. The chair 1400 includes a communications module, like the communications module 120, and a memory device, which can be part of one or more controllers, such as the controller 110. The controller 110 is programmed to create distinct pressure patterns detected from the arrays of pressure-sensitive sensors 1410, 1412, 1414a, 1414b and store the detected pressure patterns in the memory device. Each pressure pattern is indicative of seating position of each different person who sits on the chair 1400. Everyone has a unique seating position, which forms a biometric, and it is passive in the sense that the person simply interacts naturally with the chair (i.e., sits on it) without requiring any affirmative action or altering any behavior by the person. The sensors 1414a, 1414b in the armrests 1406a, 1406b detect how the person rests their elbows or arms on the armrests as further points of detection to form the unique biometric pattern.

Figure 15:
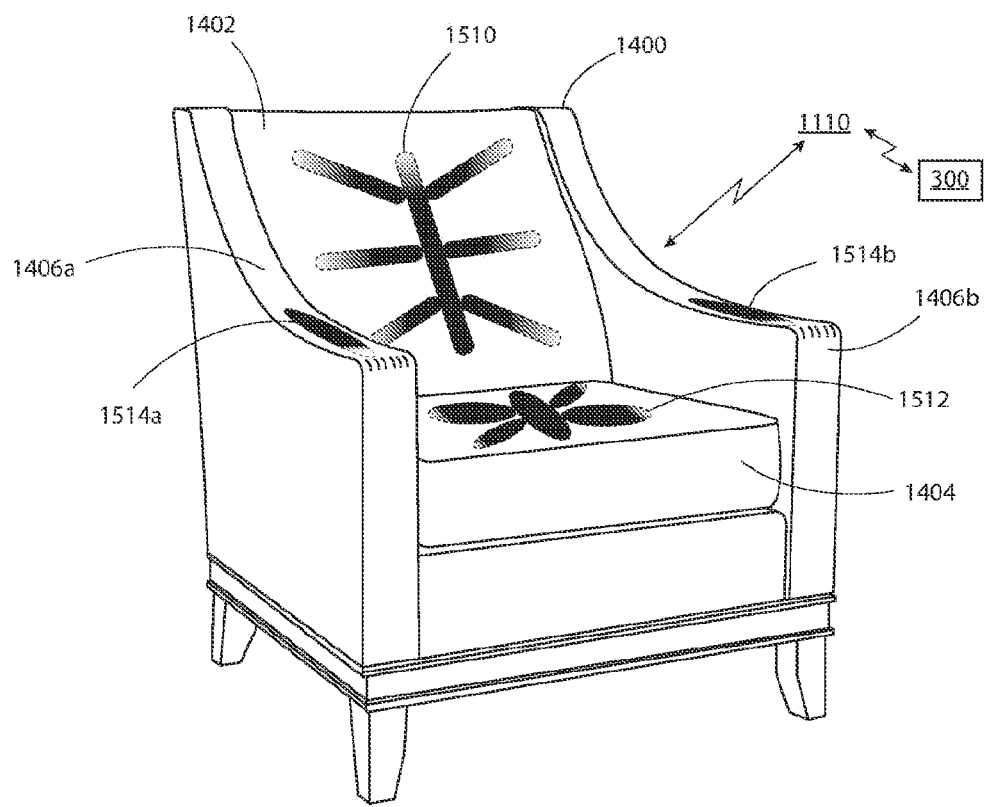
FIG. 15 is a functional diagram of an example pressure pattern that can be created via the array of pressure-sensitive sensors when one person sits in the chair, according to some implementations of the present disclosure.
Figure 16:
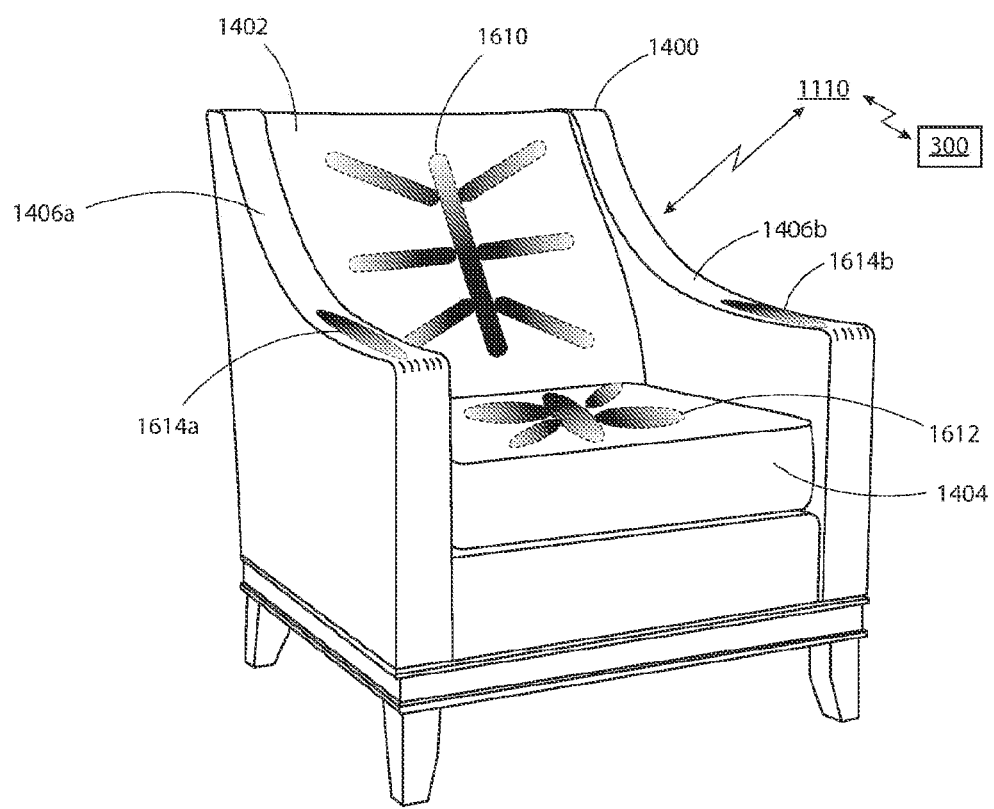
FIG. 16 is a functional diagram of another example pressure pattern that can be created via the array of pressure-sensitive sensors when a different person sits in the chair, according to some implementations of the present disclosure.

Two different example patterns (1510, 1512, 1514a, 1514b and 1610, 1612, 1614a, 1614b) are shown in FIG. 15 and FIG. 16, which represent different patterns detected by the sensors 1410, 1412, 1414a, 1414b in the chair 1400 for two different people who sit in the chair. These patterns form passive biometrics for each person, and representations of these patterns are stored in the memory device and associated with each unique individual. The darker patterns indicate a greater force or pressure being exerted on that particular area of the corresponding sensor, and lighter areas indicate a lesser force or pressure. At least the sensor 1412 in the chair seat 1404 can be used to determine a weight of the person. The output from the sensor 1410 in the chair back 1402 can also be used to calculate the weight of the person based on a distribution pattern of the weight of the person on the chair seat and the chair back.

The controller 110 can communicate from the communications module 120 the detected pressure patterns and the weights to the remote server 300 and a unique identifier associated with the chair 1400. A living facility typically has numerous chairs, and each chair is assigned a unique identifier to identify which chair is reporting the detected sensor activity. The controller 110 can identify which of the persons is sitting in the chair 1400 based on a comparison between (a) the current pressure pattern (e.g., 1510, 1512, 1514a, 1514b) detected by the pressure-sensitive sensors 1410, 1412, 1414a, 1414b and the determined weight and (b) the stored pressure patterns and the determined weights.

The controller 110 can be programmed to communicate with other furniture items that are each configured to determine a passive biometric associated with persons who interact with the furniture items. One of these furniture items can include a bed, such as a bed B shown in FIG. 4, 5A, 5B, 5C, 6A, or 6B. The bed, B, can have a mattress, embedded within which can be at least one sensor used to detect a weight of a person on the bed B and configured to communicate to the remote server 300 the detected weight of the person on the bed B.

The controller 110 and/or remote server 300 can be configured to track a person who moves from the bed B to the chair 1400 based on the detected weight of the person on the bed B, the determined weight of the person on the chair 1400, and the pressure pattern (e.g., 1510, 1512, 1514a, 1514b) created by the person on the chair 1400.

Another item of furniture can include a floor mat (not shown) having a sensor used to detect a weight of a person on the floor mat and configured to communicate to the remote server the detected weight of the person on the floor mat.

When the sensors are embedded in a bed, B, a chair 1400, and a floor mat, the controller 110 (which can be in the remote server 300), can track a person who moves among the bed B, the chair 1400, and the floor mat based on the detected weight of the person on the bed B, the detected weight of the person on the floor mat, the determined weight of the person on the chair 1400, and the pressure pattern (e.g., 1510, 1512, 1514a, 1514b) created by the person on the chair.

Having tracking movements and locations of each resident that was captured in a passive way allows the information and passive biometric capture system to produce insights that can be provided to a caregiver facility. The tracking and movement data captured by the passive biometric systems disclosed herein can be received by and blended into other existing software systems to produce personalized medical records and personalized care to each resident. The tracking data provides an additional insight into the physical movements and behaviors of each resident in a non-intrusive way. The system herein presents a smart system of sensors and software capture and analysis, which drives automated care instruction to the caregivers. From the tracking data, abnormalities or outliers from baselines can be identified and exposed, and the system can be programmed to recognize abnormalities in behavior, and provide recommendations as to what the abnormalities could be. The system can either make recommendations or take automatic action, such as automatically scheduling or adding a visit in a caregiver's schedule to a particular resident who is exhibiting anomalous behaviors that might warrant a healthcare visit or check-up. Resident dashboards used by caregivers can be modified to include outliers detected by the passive biometric capture system, so that caregivers can react in real time to baseline outliers, and detect health or comfort problems early. For example, a change in a seating posture that deviates from a baseline normal posture could indicate discomfort, or if a resident is sitting longer, this could indicate that something is bothering the resident. Having the passively captured movement and position data of each resident allows these kinds of insights to be surfaced by analyzing the data in software and providing nudges and other actionable information to caregivers on existing interfaces.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. A method of identifying outlier movement patterns of persons in a space, comprising:
   passively capturing using passive biometric sensors positions and movements of persons in a space, and associating an identity of each of the persons with a sensed movement or location using the passive biometric sensors;
   storing data indicative of the positions and movements of the persons in the space, the data including weight data associated with the persons and pressure pattern data of pressure applied by the persons to at least one item of furniture;
   baselining each of the persons positions and movements based on pattern detection from multiple data captures of the positions and movements of each of the persons;

detecting an outlier position or movement of one of the persons, which deviates from a baseline position or movement associated with the one of the persons;

communicating an indication of the outlier position or movement to a server system over a computer network.

2. The method of claim 1, further comprising:

communicating the indication of the outlier position or movement to a caregiver.

3. The method of claim 1, further comprising:

raising an alarm based at least in part on the detecting the outlier position or movement of the one of the persons.

4. The method of claim 1, wherein the passive biometric sensors include weight sensors embedded in at least one furniture item including a bed, a chair, and a floor mat, and wherein the weight data is passively captured by the weight sensors.

5. The method of claim 1, wherein the passive biometric sensors include motion sensors embedded in the at least one furniture item, the motion sensors detecting movement within a sensing range.

6. The method of claim 1, wherein the pressure pattern data is indicative of sitting positions of at least one of the persons on the at least one furniture item, wherein the at least one furniture item includes a chair.

\* \* \* \* \*